US010342632B2

(12) United States Patent
Andrews et al.

(10) Patent No.: US 10,342,632 B2
(45) Date of Patent: Jul. 9, 2019

(54) IMAGE-GUIDED THERAPY OF A TISSUE

(71) Applicant: MONTERIS MEDICAL CORPORATION, Plymouth, MN (US)

(72) Inventors: Eric Andrews, St. Anthony, MN (US); Mark Grant, Winnipeg (CA); Brooke Ren, Maple Grove, MN (US); Richard Tyc, Winnipeg (CA)

(73) Assignee: MONTERIS MEDICAL CORPORATION, Plymouth, MN (US)

( * ) Notice: Subject to any disclaimer, the term of this patent is extended or adjusted under 35 U.S.C. 154(b) by 284 days.

(21) Appl. No.: 15/254,290

(22) Filed: Sep. 1, 2016

(65) Prior Publication Data
US 2016/0367333 A1 Dec. 22, 2016

Related U.S. Application Data

(63) Continuation of application No. 14/661,138, filed on Mar. 18, 2015, now Pat. No. 9,433,383.
(Continued)

(51) Int. Cl.
*A61B 6/04* (2006.01)
*A61F 5/37* (2006.01)
(Continued)

(52) U.S. Cl.
CPC ............ *A61B 90/14* (2016.02); *A61B 5/0042* (2013.01); *A61B 5/015* (2013.01); *A61B 5/0555* (2013.01);
(Continued)

(58) Field of Classification Search
CPC . A61F 5/37; A61F 5/3707; A61B 6/04; A61B 6/0421; A61B 6/0428;
(Continued)

(56) References Cited

U.S. PATENT DOCUMENTS 3,021,842 A 2/1962 Flood
3,139,990 A 7/1964 Jelatis et al.
(Continued)

FOREIGN PATENT DOCUMENTS

CA 2348867 A1 5/2000
CA 2370222 A1 10/2000
(Continued)

OTHER PUBLICATIONS

Office Action dated Jul. 5, 2016 in Chinese Patent Application No. 201380043974.1.
(Continued)

*Primary Examiner* — Keri J Nelson
(74) *Attorney, Agent, or Firm* — Fox Rothschild LLP

(57) ABSTRACT

In one aspect, the present disclosure relates to a head fixation apparatus including a number of support posts, and a curved ring portion including a number of connectors configured to adjustably and releasably mount support posts on the lower ring portion, such that the support posts are selectively mounted to a subset of the connectors in a customized arrangement for a patient. The apparatus may include a ring mount configured for fixation to a platform, including a curved channel substantially matching a curvature of the curved ring portion, and a mount locking mechanism for locking the curved ring portion within the channel of the ring mount. The curved ring portion may be configured to rotate within the channel of the ring mount while the ring mount is fixed to the platform, an angular head position of the patient being selectably adjustable while the patient is laying on the platform.

8 Claims, 16 Drawing Sheets

Related U.S. Application Data

(60) Provisional application No. 61/955,124, filed on Mar. 18, 2014.

(51) Int. Cl.

| | | |
|---|---|---|
| A61N 5/10 | (2006.01) | |
| A61B 90/14 | (2016.01) | |
| A61B 5/00 | (2006.01) | |
| A61B 5/055 | (2006.01) | |
| A61B 17/17 | (2006.01) | |
| A61B 5/01 | (2006.01) | |
| A61B 17/34 | (2006.01) | |
| A61B 18/04 | (2006.01) | |
| A61B 18/14 | (2006.01) | |
| A61B 34/20 | (2016.01) | |
| A61B 90/50 | (2016.01) | |
| A61B 90/11 | (2016.01) | |
| A61B 34/10 | (2016.01) | |
| A61B 90/00 | (2016.01) | |
| A61B 6/03 | (2006.01) | |
| A61B 18/22 | (2006.01) | |
| A61N 5/06 | (2006.01) | |
| A61N 7/02 | (2006.01) | |
| A61B 17/00 | (2006.01) | |
| A61B 18/20 | (2006.01) | |
| A61N 7/00 | (2006.01) | |
| A61B 90/10 | (2016.01) | |
| A61B 18/00 | (2006.01) | |
| A61B 18/02 | (2006.01) | |
| A61B 18/18 | (2006.01) | |

(52) U.S. Cl.
CPC ............ *A61B 5/4839* (2013.01); *A61B 5/702* (2013.01); *A61B 5/742* (2013.01); *A61B 5/748* (2013.01); *A61B 6/032* (2013.01); *A61B 6/04* (2013.01); *A61B 6/0421* (2013.01); *A61B 6/0492* (2013.01); *A61B 17/00234* (2013.01); *A61B 17/1703* (2013.01); *A61B 17/1739* (2013.01); *A61B 17/3403* (2013.01); *A61B 18/04* (2013.01); *A61B 18/1477* (2013.01); *A61B 18/1492* (2013.01); *A61B 18/22* (2013.01); *A61B 34/10* (2016.02); *A61B 34/20* (2016.02); *A61B 90/11* (2016.02); *A61B 90/37* (2016.02); *A61B 90/50* (2016.02); *A61F 5/37* (2013.01); *A61F 5/3707* (2013.01); *A61N 5/062* (2013.01); *A61N 7/02* (2013.01); *A61N 7/022* (2013.01); *A61B 5/0035* (2013.01); *A61B 5/01* (2013.01); *A61B 5/055* (2013.01); *A61B 2018/00011* (2013.01); *A61B 2018/00321* (2013.01); *A61B 2018/00446* (2013.01); *A61B 2018/00791* (2013.01); *A61B 2018/0293* (2013.01); *A61B 2018/1869* (2013.01); *A61B 2018/20361* (2017.05); *A61B 2034/107* (2016.02); *A61B 2034/2051* (2016.02); *A61B 2034/2065* (2016.02); *A61B 2090/103* (2016.02); *A61B 2090/374* (2016.02); *A61B 2090/3954* (2016.02); *A61B 2576/026* (2013.01); *A61N 5/1048* (2013.01); *A61N 2005/1051* (2013.01); *A61N 2005/1055* (2013.01); *A61N 2005/1097* (2013.01); *A61N 2007/003* (2013.01); *A61N 2007/0047* (2013.01); *A61N 2007/025* (2013.01)

(58) Field of Classification Search
CPC ..... A61B 6/0492; A61B 19/203; A61B 90/14; A61N 5/1048; A61N 5/1049; A61N 2005/1051; A61N 2005/1055; A61N 2005/1097

USPC ........ 128/845, 846, 869; 600/410, 414–417; 606/130; 5/601, 622, 637
See application file for complete search history.

(56) References Cited

U.S. PATENT DOCUMENTS

| | | | |
|---|---|---|---|
| 4,111,209 A | 9/1978 | Wolvek et al. | |
| 4,233,979 A | 11/1980 | Naser | |
| 4,360,028 A | 11/1982 | Barbier et al. | |
| 4,378,016 A | 3/1983 | Loeb | |
| 4,402,694 A | 9/1983 | Ash et al. | |
| 4,568,559 A | 2/1986 | Nuwayser et al. | |
| 4,609,174 A | 9/1986 | Nakatani | |
| 4,622,953 A | 11/1986 | Gordon | |
| 4,623,588 A | 11/1986 | Nuwayser et al. | |
| 4,646,752 A | 3/1987 | Swann et al. | |
| 4,671,254 A | 6/1987 | Fair | |
| 4,733,660 A | 3/1988 | Itzkan | |
| 4,733,929 A | 3/1988 | Brown | |
| 4,832,024 A | 5/1989 | Boussignac et al. | |
| 4,914,608 A | 4/1990 | LeBihan et al. | |
| 4,986,628 A | 1/1991 | Lozhenko et al. | |
| 5,059,415 A | 10/1991 | Neuwelt | |
| 5,078,140 A | 1/1992 | Kwoh | |
| 5,085,219 A | 2/1992 | Ortendahl et al. | |
| 5,092,891 A | 3/1992 | Kummer et al. | |
| 5,102,410 A | 4/1992 | Dressel | |
| 5,116,344 A | 5/1992 | Sundqvist | |
| 5,154,723 A | 10/1992 | Kubota et al. | |
| 5,192,278 A | 3/1993 | Hayes et al. | |
| 5,196,005 A | 3/1993 | Doiron et al. | |
| 5,201,742 A | 4/1993 | Hasson | |
| 5,207,669 A | 5/1993 | Baker et al. | |
| 5,207,681 A | 5/1993 | Ghadjar et al. | |
| 5,217,441 A | 6/1993 | Shichman | |
| 5,222,953 A | 6/1993 | Dowlatshahi | |
| 5,230,338 A | 7/1993 | Allen et al. | |
| 5,242,438 A | 9/1993 | Saadatmanesh et al. | |
| 5,246,436 A | 9/1993 | Rowe | |
| 5,247,935 A | 9/1993 | Cline et al. | |
| 5,263,956 A | 11/1993 | Nobles | |
| 5,269,777 A | 12/1993 | Doiron et al. | |
| 5,275,165 A | 1/1994 | Ettinger et al. | |
| 5,281,213 A | 1/1994 | Milder et al. | |
| 5,284,144 A | 2/1994 | Delannoy | |
| 5,291,890 A | 3/1994 | Cline et al. | |
| 5,292,320 A | 3/1994 | Brown et al. | |
| 5,307,144 A | 4/1994 | Hiroshi et al. | |
| 5,307,812 A | 5/1994 | Hardy et al. | |
| 5,312,351 A | 5/1994 | Gerrone | |
| 5,320,617 A | 6/1994 | Leach | |
| 5,323,779 A | 6/1994 | Hardy et al. | |
| 5,327,884 A | 7/1994 | Hardy et al. | |
| 5,343,543 A | 8/1994 | Noval, Jr. et al. | |
| 5,344,419 A | 9/1994 | Spears | |
| 5,348,048 A | 9/1994 | Schirado | |
| 5,354,293 A | 10/1994 | Beyer et al. | |
| 5,354,294 A | 10/1994 | Chou | |
| 5,366,456 A | 11/1994 | Rink et al. | |
| 5,368,031 A | 11/1994 | Cline et al. | |
| 5,368,032 A | 11/1994 | Cline et al. | |
| 5,370,649 A | 12/1994 | Gardetto et al. | |
| 5,374,266 A | 12/1994 | Kataoka et al. | |
| 5,387,220 A | 2/1995 | Pisharodi | |
| 5,388,580 A | 2/1995 | Sullivan et al. | |
| 5,409,493 A | 4/1995 | Greenberg | |
| 5,433,717 A | 7/1995 | Rubinsky et al. | |
| 5,443,068 A | 8/1995 | Cline et al. | |
| 5,445,166 A | 8/1995 | Taylor | |
| 5,454,794 A | 10/1995 | Narciso et al. | |
| 5,454,807 A | 10/1995 | Lennox | |
| 5,454,897 A | 10/1995 | Vaniglia | |
| 5,469,353 A | 11/1995 | Pinsky et al. | |
| 5,474,564 A | 12/1995 | Clayman et al. | |
| 5,476,461 A | 12/1995 | Cho et al. | |
| 5,490,840 A | 2/1996 | Uzgiris et al. | |

(56) References Cited

U.S. PATENT DOCUMENTS

| | | |
|---|---|---|
| 5,492,122 A | 2/1996 | Button et al. |
| 5,496,308 A | 3/1996 | Brown et al. |
| 5,499,313 A | 3/1996 | Kleinerman |
| 5,509,917 A | 4/1996 | Cecchetti et al. |
| 5,526,814 A | 6/1996 | Cline et al. |
| 5,530,780 A | 6/1996 | Ohsawa |
| 5,534,000 A | 7/1996 | Bruce |
| 5,537,499 A | 7/1996 | Brekke |
| 5,553,618 A | 9/1996 | Suzuki et al. |
| 5,562,688 A | 10/1996 | Riza |
| 5,568,503 A | 10/1996 | Omori |
| 5,571,099 A | 11/1996 | Purcell, Jr. et al. |
| 5,589,233 A | 12/1996 | Law et al. |
| 5,590,653 A | 1/1997 | Aida et al. |
| 5,620,479 A | 4/1997 | Diederich |
| 5,632,767 A | 5/1997 | Sinofsky |
| 5,636,259 A | 6/1997 | Khutoryansky et al. |
| 5,638,819 A | 6/1997 | Manwaring et al. |
| 5,643,179 A | 7/1997 | Fujimoto |
| 5,647,361 A | 7/1997 | Damadian |
| 5,655,084 A | 8/1997 | Pinsky et al. |
| 5,657,760 A | 8/1997 | Ying et al. |
| 5,663,646 A | 9/1997 | Kuth et al. |
| 5,671,353 A | 9/1997 | Tian et al. |
| 5,672,171 A | 9/1997 | Andrus et al. |
| 5,672,172 A | 9/1997 | Zupkas |
| 5,695,501 A | 12/1997 | Carol et al. |
| 5,711,300 A | 1/1998 | Schneider et al. |
| 5,715,823 A | 2/1998 | Wood et al. |
| 5,716,369 A | 2/1998 | Riza |
| 5,719,975 A | 2/1998 | Wolfson et al. |
| 5,728,106 A | 3/1998 | Misko et al. |
| 5,733,277 A | 3/1998 | Pallarito |
| 5,735,846 A | 4/1998 | Panescu et al. |
| 5,749,362 A | 5/1998 | Funda et al. |
| 5,749,549 A | 5/1998 | Ashjaee |
| 5,752,962 A | 5/1998 | D'Urso |
| 5,762,066 A | 6/1998 | Law et al. |
| 5,769,790 A | 6/1998 | Watkins et al. |
| 5,772,657 A | 6/1998 | Hmelar et al. |
| 5,785,704 A | 7/1998 | Bille |
| 5,792,110 A | 8/1998 | Cunningham |
| 5,807,383 A | 9/1998 | Kolesa et al. |
| 5,814,008 A | 9/1998 | Chen et al. |
| 5,817,036 A | 10/1998 | Anthony et al. |
| 5,823,941 A | 10/1998 | Shaunnessey |
| 5,824,005 A | 10/1998 | Motamedi et al. |
| 5,830,209 A | 11/1998 | Savage et al. |
| 5,848,967 A | 12/1998 | Cosman |
| 5,855,582 A | 1/1999 | Gildenberg |
| 5,855,583 A | 1/1999 | Wang et al. |
| 5,861,020 A | 1/1999 | Schwarzmaier |
| 5,873,845 A | 2/1999 | Cline et al. |
| 5,874,955 A | 2/1999 | Rogowitz et al. |
| 5,876,342 A | 3/1999 | Chen et al. |
| 5,890,897 A | 4/1999 | Kruger et al. |
| 5,891,100 A | 4/1999 | Fleckenstein |
| 5,891,157 A | 4/1999 | Day et al. |
| 5,897,495 A | 4/1999 | Aida et al. |
| 5,916,161 A | 6/1999 | Ishihara et al. |
| 5,928,145 A | 7/1999 | Ocali et al. |
| 5,944,663 A | 8/1999 | Kuth et al. |
| 5,945,827 A | 8/1999 | Gronauer et al. |
| 5,947,958 A | 9/1999 | Woodard et al. |
| 5,949,929 A | 9/1999 | Hamm |
| 5,959,246 A | 9/1999 | Gretz |
| 5,961,466 A | 10/1999 | Anbar |
| 5,978,541 A | 11/1999 | Doiron et al. |
| 5,989,246 A | 11/1999 | Kaufmann et al. |
| 5,993,463 A | 11/1999 | Truwit |
| 6,004,315 A | 12/1999 | Dumont |
| 6,006,126 A | 12/1999 | Cosman |
| 6,019,724 A | 2/2000 | Gronningsaeter et al. |
| 6,022,309 A | 2/2000 | Celliers et al. |
| 6,039,728 A | 3/2000 | Berlien et al. |
| 6,047,216 A | 4/2000 | Carl et al. |
| 6,050,943 A | 4/2000 | Slayton et al. |
| 6,053,912 A | 4/2000 | Panescu et al. |
| 6,058,323 A | 5/2000 | Lemelson |
| 6,067,371 A | 5/2000 | Gouge et al. |
| 6,071,288 A | 6/2000 | Carol et al. |
| 6,081,533 A | 6/2000 | Laubach et al. |
| 6,086,532 A | 7/2000 | Panescu et al. |
| 6,106,516 A | 8/2000 | Massengill |
| 6,117,143 A | 9/2000 | Hynes et al. |
| 6,123,719 A | 9/2000 | Masychev |
| 6,128,522 A | 10/2000 | Acker et al. |
| 6,131,480 A | 10/2000 | Yoneyama |
| 6,132,437 A | 10/2000 | Omurtag et al. |
| 6,133,306 A | 10/2000 | Beal |
| 6,143,018 A | 11/2000 | Beuthan et al. |
| 6,148,225 A | 11/2000 | Kestler et al. |
| 6,151,404 A | 11/2000 | Pieper |
| 6,152,933 A | 11/2000 | Werp et al. |
| 6,159,150 A | 12/2000 | Yale et al. |
| 6,162,052 A | 12/2000 | Kokubu |
| 6,164,843 A | 12/2000 | Battocchio |
| 6,167,295 A | 12/2000 | Cosman |
| 6,179,831 B1 | 1/2001 | Bliweis |
| 6,195,579 B1 | 2/2001 | Carroll et al. |
| 6,206,873 B1 | 3/2001 | Paolini et al. |
| 6,206,885 B1 | 3/2001 | Ghahremani et al. |
| 6,206,890 B1 | 3/2001 | Truwit |
| 6,226,680 B1 | 5/2001 | Boucher et al. |
| 6,241,725 B1 | 6/2001 | Cosman |
| 6,246,200 B1 | 6/2001 | Blumenkranz et al. |
| 6,246,896 B1 | 6/2001 | Dumoulin et al. |
| 6,246,912 B1 | 6/2001 | Sluijter et al. |
| 6,254,043 B1 | 7/2001 | Schwärzler |
| 6,263,229 B1 | 7/2001 | Atalar et al. |
| 6,267,769 B1 | 7/2001 | Truwit |
| 6,267,770 B1 | 7/2001 | Truwit |
| 6,280,384 B1 | 8/2001 | Loeffler |
| 6,283,958 B1 | 9/2001 | Vogl et al. |
| 6,283,988 B1 | 9/2001 | Laufer et al. |
| 6,286,795 B1 | 9/2001 | Johnson |
| 6,293,282 B1 | 9/2001 | Lemelson |
| 6,320,928 B1 | 11/2001 | Vaillant et al. |
| 6,321,266 B1 | 11/2001 | Yokomizo et al. |
| 6,332,891 B1 | 12/2001 | Himes |
| 6,334,847 B1 | 1/2002 | Fenster et al. |
| 6,353,445 B1 | 3/2002 | Babula et al. |
| 6,355,028 B2 | 3/2002 | Castaneda et al. |
| 6,368,329 B1 | 4/2002 | Truwit |
| 6,368,330 B1 | 4/2002 | Hynes et al. |
| 6,397,098 B1 | 5/2002 | Uber, III et al. |
| 6,398,778 B1 | 6/2002 | Gu et al. |
| 6,409,722 B1 | 6/2002 | Hoey et al. |
| 6,413,253 B1 | 7/2002 | Koop |
| 6,413,263 B1 | 7/2002 | Lobdill et al. |
| 6,416,520 B1 | 7/2002 | Kynast et al. |
| 6,418,337 B1 | 7/2002 | Torchia |
| 6,419,648 B1 | 7/2002 | Vitek et al. |
| 6,423,057 B1 | 7/2002 | He et al. |
| 6,423,077 B2 | 7/2002 | Carol et al. |
| 6,425,867 B1 | 7/2002 | Vaezy et al. |
| 6,440,127 B2 | 8/2002 | McGovern et al. |
| 6,447,505 B2 | 9/2002 | McGovern et al. |
| 6,451,015 B1 | 9/2002 | Rittman, III et al. |
| 6,454,774 B1 | 9/2002 | Fleckenstein |
| 6,461,314 B1 | 10/2002 | Pant et al. |
| 6,464,690 B1 | 10/2002 | Castaneda et al. |
| 6,464,691 B1 | 10/2002 | Castaneda et al. |
| 6,464,694 B1 | 10/2002 | Massengill |
| 6,468,238 B1 | 10/2002 | Hawkins et al. |
| 6,488,697 B1 | 12/2002 | Ariura et al. |
| 6,491,699 B1 | 12/2002 | Henderson et al. |
| 6,501,978 B2 | 12/2002 | Wagshul et al. |
| 6,506,154 B1 | 1/2003 | Ezion et al. |
| 6,506,171 B1 | 1/2003 | Vitek et al. |
| 6,507,747 B1 | 1/2003 | Gowda et al. |
| 6,510,241 B1 | 1/2003 | Vaillant et al. |
| 6,522,142 B1 | 2/2003 | Freundlich |
| 6,522,913 B2 | 2/2003 | Swanson et al. |

(56) References Cited

U.S. PATENT DOCUMENTS

| | | |
|---|---|---|
| 6,529,765 B1 | 3/2003 | Franck et al. |
| 6,542,767 B1 | 4/2003 | McNichols et al. |
| 6,543,272 B1 | 4/2003 | Vitek |
| 6,544,248 B1 | 4/2003 | Bass |
| 6,544,257 B2 | 4/2003 | Nagase et al. |
| 6,549,800 B1 | 4/2003 | Atalar et al. |
| 6,551,274 B2 | 4/2003 | Heiner |
| 6,554,826 B1 | 4/2003 | Deardorff |
| 6,558,375 B1 | 5/2003 | Sinofsky et al. |
| 6,559,644 B2 | 5/2003 | Froundlich et al. |
| 6,577,888 B1 | 6/2003 | Chan et al. |
| 6,579,281 B2 | 6/2003 | Palmer et al. |
| 6,582,381 B1 | 6/2003 | Yehezkeli et al. |
| 6,582,420 B2 | 6/2003 | Castaneda et al. |
| 6,585,665 B1 | 7/2003 | Chapman et al. |
| 6,589,174 B1 | 7/2003 | Chopra et al. |
| 6,591,128 B1 | 7/2003 | Wu et al. |
| 6,603,988 B2 | 8/2003 | Dowlatshahi |
| 6,606,091 B2 | 8/2003 | Liang et al. |
| 6,606,513 B2 | 8/2003 | Lardo et al. |
| 6,612,988 B2 | 9/2003 | Maor et al. |
| 6,613,004 B1 | 9/2003 | Vitek et al. |
| 6,613,005 B1 | 9/2003 | Friedman et al. |
| 6,618,608 B1 | 9/2003 | Watkins et al. |
| 6,618,620 B1 | 9/2003 | Freundlich et al. |
| 6,623,490 B1 | 9/2003 | Crane et al. |
| 6,626,854 B2 | 9/2003 | Friedman et al. |
| 6,628,980 B2 | 9/2003 | Atalar et al. |
| 6,631,499 B1 | 10/2003 | Tsujii |
| 6,645,162 B2 | 11/2003 | Friedman et al. |
| 6,666,833 B1 | 12/2003 | Friedman et al. |
| 6,671,535 B1 | 12/2003 | McNichols et al. |
| 6,675,033 B1 | 1/2004 | Lardo et al. |
| 6,675,037 B1 | 1/2004 | Tsekos |
| 6,684,097 B1 | 1/2004 | Parel et al. |
| 6,695,871 B1 | 2/2004 | Maki et al. |
| 6,701,176 B1 | 3/2004 | Halperin et al. |
| 6,701,181 B2 | 3/2004 | Tang et al. |
| 6,705,994 B2 | 3/2004 | Vortman et al. |
| 6,716,215 B1 | 4/2004 | David et al. |
| 6,731,966 B1 | 5/2004 | Spigelman et al. |
| 6,735,461 B2 | 5/2004 | Vitek et al. |
| 6,741,883 B2 | 5/2004 | Gildenberg |
| 6,752,812 B1 | 6/2004 | Truwit |
| 6,755,849 B1 | 6/2004 | Gowda et al. |
| 6,770,031 B2 | 8/2004 | Hynynen et al. |
| 6,773,408 B1 | 8/2004 | Acker et al. |
| 6,782,288 B2 | 8/2004 | Truwit et al. |
| 6,790,180 B2 | 9/2004 | Vitek |
| 6,801,643 B2 | 10/2004 | Pieper |
| 6,823,216 B1 | 11/2004 | Salomir et al. |
| 6,825,838 B2 | 11/2004 | Smith et al. |
| 6,843,793 B2 | 1/2005 | Brock et al. |
| 6,845,193 B2 | 1/2005 | Loeb et al. |
| 6,893,447 B2 | 5/2005 | Dominguez et al. |
| 6,898,454 B2 | 5/2005 | Atalar et al. |
| 6,902,569 B2 | 6/2005 | Parmer et al. |
| 6,904,307 B2 | 6/2005 | Karmarkar et al. |
| 6,986,764 B2 | 1/2006 | Davenport et al. |
| 7,033,367 B2 | 4/2006 | Ghahremani et al. |
| 7,072,704 B2 | 7/2006 | Bucholz |
| 7,074,233 B1 | 7/2006 | Gowda et al. |
| 7,097,641 B1 | 8/2006 | Arless et al. |
| 7,123,255 B2 | 10/2006 | Trousett et al. |
| 7,128,711 B2 | 10/2006 | Medan et al. |
| 7,133,714 B2 | 11/2006 | Karmarkar et al. |
| 7,163,542 B2 | 1/2007 | Ryan |
| 7,164,940 B2 | 1/2007 | Hareyama et al. |
| 7,166,458 B2 | 1/2007 | Ballerstadt et al. |
| 7,167,741 B2 | 1/2007 | Torchia et al. |
| 7,167,760 B2 | 1/2007 | Dawant et al. |
| 7,175,596 B2 | 2/2007 | Vitek et al. |
| 7,226,414 B2 | 6/2007 | Ballerstadt et al. |
| 7,228,165 B1 | 6/2007 | Sullivan |
| 7,229,451 B2 | 6/2007 | Day et al. |
| 7,235,084 B2 | 6/2007 | Shakoon et al. |
| 7,235,089 B1 | 6/2007 | McGuckin, Jr. |
| 7,236,812 B1 | 6/2007 | Ballerstadt et al. |
| 7,236,816 B2 | 6/2007 | Kumar et al. |
| 7,270,656 B2 | 9/2007 | Gowda et al. |
| 7,274,847 B2 | 9/2007 | Gowda et al. |
| 7,280,686 B2 | 10/2007 | Hornegger et al. |
| 7,292,719 B2 | 11/2007 | Arnon |
| 7,315,167 B2 | 1/2008 | Bottcher et al. |
| 7,321,374 B2 | 1/2008 | Naske |
| 7,344,529 B2 | 3/2008 | Torchia et al. |
| RE40,279 E | 4/2008 | Sluijter et al. |
| 7,366,561 B2 | 4/2008 | Mills et al. |
| 7,371,210 B2 | 5/2008 | Brock et al. |
| 7,377,900 B2 | 5/2008 | Vitek et al. |
| 7,412,141 B2 | 8/2008 | Gowda et al. |
| 7,450,985 B2 | 11/2008 | Meloy et al. |
| 7,463,801 B2 | 12/2008 | Brekke et al. |
| 7,479,139 B2 | 1/2009 | Cytron et al. |
| 7,489,133 B1 | 2/2009 | Keidl et al. |
| 7,494,489 B2 | 2/2009 | Roh |
| 7,507,244 B2 | 3/2009 | Dinkler et al. |
| 7,519,210 B2 | 4/2009 | Hirsch et al. |
| 7,521,930 B2 | 4/2009 | Li et al. |
| 7,535,794 B2 | 5/2009 | Prus et al. |
| 7,551,953 B2 | 6/2009 | Lardo et al. |
| 7,561,906 B2 | 7/2009 | Atalar et al. |
| 7,599,729 B2 | 10/2009 | Atalar et al. |
| 7,602,190 B2 | 10/2009 | Piferi et al. |
| 7,609,927 B2 | 10/2009 | Gowda et al. |
| 7,611,462 B2 | 11/2009 | Vortman et al. |
| 7,631,233 B2 | 12/2009 | Parris et al. |
| 7,634,119 B2 | 12/2009 | Tsougarakis et al. |
| 7,652,410 B2 | 1/2010 | Prus |
| 7,659,719 B2 | 2/2010 | Vaughan et al. |
| 7,661,162 B2 | 2/2010 | Soerensen et al. |
| 7,699,780 B2 | 4/2010 | Vitek et al. |
| 7,702,140 B2 | 4/2010 | Hirsch et al. |
| 7,706,858 B1 | 4/2010 | Green et al. |
| 7,717,853 B2 | 5/2010 | Nita et al. |
| 7,736,371 B2 | 6/2010 | Schoepp |
| 7,778,682 B2 | 8/2010 | Kumar et al. |
| 7,792,566 B2 | 9/2010 | Roland et al. |
| 7,794,469 B2 | 9/2010 | Kao et al. |
| 7,801,587 B2 | 9/2010 | Webber et al. |
| 7,848,788 B2 | 12/2010 | Tulley et al. |
| 7,876,939 B2 | 1/2011 | Yankelevitz et al. |
| 7,925,328 B2 | 4/2011 | Urquhart et al. |
| 7,957,783 B2 | 6/2011 | Atalar et al. |
| 8,002,706 B2 | 8/2011 | Vortman et al. |
| 8,022,705 B2 | 9/2011 | Bogdanov et al. |
| RE42,856 E | 10/2011 | Karmarkar et al. |
| 8,029,471 B1 | 10/2011 | Sahibzada et al. |
| 8,034,569 B2 | 10/2011 | Jackson et al. |
| 8,055,351 B2 | 11/2011 | Atalar et al. |
| 8,060,182 B2 | 11/2011 | He et al. |
| 8,068,893 B2 | 11/2011 | Guttman et al. |
| 8,088,067 B2 | 1/2012 | Vortman et al. |
| 8,094,900 B2 | 1/2012 | Steines et al. |
| 8,099,150 B2 | 1/2012 | Piferi et al. |
| 8,100,132 B2 | 1/2012 | Markstroem et al. |
| 8,108,028 B2 | 1/2012 | Karmarkar |
| 8,114,068 B2 | 2/2012 | Rheinwald et al. |
| 8,116,843 B2 | 2/2012 | Dai et al. |
| 8,157,828 B2 | 4/2012 | Piferi |
| 8,165,658 B2 | 4/2012 | Waynik et al. |
| 8,175,677 B2 | 5/2012 | Sayler et al. |
| 8,190,237 B2 | 5/2012 | Driemel et al. |
| 8,195,272 B2 | 6/2012 | Piferi et al. |
| 8,208,993 B2 | 6/2012 | Piferi et al. |
| 8,211,095 B2 | 7/2012 | Gowda et al. |
| 8,216,854 B2 | 7/2012 | Ballerstadt et al. |
| 8,221,427 B2 | 7/2012 | Roh |
| 8,224,420 B2 | 7/2012 | Mu et al. |
| 8,233,701 B2 | 7/2012 | Frakes et al. |
| 8,235,901 B2 | 8/2012 | Schmidt et al. |
| 8,251,908 B2 | 8/2012 | Vortman et al. |
| 8,267,938 B2 | 9/2012 | Murphy |
| 8,270,698 B2 | 9/2012 | Geiger |

(56) References Cited

U.S. PATENT DOCUMENTS

| | | |
|---|---|---|
| 8,285,097 B2 | 10/2012 | Griffin |
| 8,287,537 B2 | 10/2012 | Dinkler |
| 8,298,245 B2 | 10/2012 | Li et al. |
| 8,314,052 B2 | 11/2012 | Jackson |
| 8,315,689 B2 | 11/2012 | Jenkins et al. |
| 8,320,990 B2 | 11/2012 | Vij |
| 8,340,743 B2 | 12/2012 | Jenkins et al. |
| RE43,901 E | 1/2013 | Freundlich et al. |
| 8,343,138 B2 | 1/2013 | Asfora |
| 8,364,217 B2 | 1/2013 | Ballerstadt et al. |
| 8,368,401 B2 | 2/2013 | Levy et al. |
| 8,369,930 B2 | 2/2013 | Jenkins et al. |
| 8,374,677 B2 | 2/2013 | Piferi et al. |
| 8,380,277 B2 | 2/2013 | Atalar et al. |
| 8,387,220 B2 | 3/2013 | Ishikura et al. |
| 8,396,532 B2 | 3/2013 | Jenkins et al. |
| 8,404,495 B2 | 3/2013 | Ballerstadt et al. |
| 8,409,099 B2 | 4/2013 | Vitek et al. |
| 8,414,597 B2 | 4/2013 | Kao et al. |
| 8,425,424 B2 | 4/2013 | Zadicario et al. |
| 8,433,421 B2 | 4/2013 | Atalar et al. |
| 8,482,285 B2 | 7/2013 | Grissom et al. |
| 8,520,932 B2 | 8/2013 | Cool et al. |
| 8,548,561 B2 | 10/2013 | Vortman et al. |
| 8,548,569 B2 | 10/2013 | Piferi et al. |
| 8,608,672 B2 | 12/2013 | Vortman et al. |
| 8,617,073 B2 | 12/2013 | Prus et al. |
| RE44,726 E | 1/2014 | Parris et al. |
| RE44,736 E | 1/2014 | Karmarkar et al. |
| 8,644,906 B2 | 2/2014 | Piferi et al. |
| 8,649,842 B2 | 2/2014 | Atalar et al. |
| 8,661,873 B2 | 3/2014 | Medan et al. |
| 8,688,226 B2 | 4/2014 | Atalar et al. |
| 8,737,712 B2 | 5/2014 | Geiger |
| 2001/0003798 A1 | 6/2001 | McGovern et al. |
| 2002/0019641 A1 | 2/2002 | Truwit |
| 2002/0042605 A1 | 4/2002 | Castaneda et al. |
| 2002/0052610 A1 | 5/2002 | Skakoon et al. |
| 2002/0087148 A1 | 7/2002 | Brock et al. |
| 2002/0169460 A1 | 11/2002 | Foster et al. |
| 2002/0177843 A1 | 11/2002 | Anderson et al. |
| 2003/0023236 A1 | 1/2003 | Gowda et al. |
| 2003/0060813 A1 | 3/2003 | Loeb et al. |
| 2003/0171741 A1 | 9/2003 | Ziebol et al. |
| 2003/0187371 A1 | 10/2003 | Vortman et al. |
| 2004/0073100 A1 | 4/2004 | Ballerstadt et al. |
| 2004/0075031 A1 | 4/2004 | Crain et al. |
| 2004/0122446 A1 | 6/2004 | Solar |
| 2004/0123870 A1 | 7/2004 | Stamper et al. |
| 2004/0133190 A1 | 7/2004 | Hobart et al. |
| 2004/0134884 A1 | 7/2004 | Wei et al. |
| 2004/0167542 A1 | 8/2004 | Solar et al. |
| 2004/0167543 A1 | 8/2004 | Mazzocchi et al. |
| 2004/0267284 A1 | 12/2004 | Parmer et al. |
| 2005/0070920 A1 | 3/2005 | Solar et al. |
| 2005/0154378 A1 | 7/2005 | Teague et al. |
| 2006/0009749 A1 | 1/2006 | Weckwerth et al. |
| 2006/0089626 A1 | 4/2006 | Vlegele et al. |
| 2006/0122590 A1 | 6/2006 | Bliweis et al. |
| 2006/0122629 A1 | 6/2006 | Skakoon |
| 2006/0175484 A1 | 8/2006 | Wood, III et al. |
| 2006/0192319 A1 | 8/2006 | Solar et al. |
| 2006/0195119 A1 | 8/2006 | Mazzocchi et al. |
| 2006/0206105 A1 | 9/2006 | Chopra et al. |
| 2006/0212044 A1 | 9/2006 | Bova et al. |
| 2006/0229641 A1 | 10/2006 | Gupta et al. |
| 2006/0241393 A1 | 10/2006 | Liu et al. |
| 2006/0287647 A1 | 12/2006 | Torchia et al. |
| 2007/0016039 A1 | 1/2007 | Vortman et al. |
| 2007/0043342 A1 | 2/2007 | Kleinberger |
| 2007/0088416 A1 | 4/2007 | Atalar et al. |
| 2007/0100346 A1 | 5/2007 | Wyss et al. |
| 2007/0106305 A1 | 5/2007 | Kao et al. |
| 2007/0149977 A1 | 6/2007 | Heavener |
| 2007/0191867 A1 | 8/2007 | Mazzocchi et al. |
| 2007/0197918 A1 | 8/2007 | Vitek et al. |
| 2007/0208352 A1 | 9/2007 | Henderson et al. |
| 2007/0225562 A1 | 9/2007 | Spivey et al. |
| 2007/0238978 A1 | 10/2007 | Kumar et al. |
| 2007/0239062 A1 | 10/2007 | Chopra et al. |
| 2007/0250077 A1 | 10/2007 | Skakoon et al. |
| 2007/0270717 A1 | 11/2007 | Tang et al. |
| 2007/0282404 A1 | 12/2007 | Cottrell et al. |
| 2008/0002927 A1 | 1/2008 | Furnish |
| 2008/0027463 A1 | 1/2008 | Labadie et al. |
| 2008/0033278 A1 | 2/2008 | Assif |
| 2008/0033292 A1 | 2/2008 | Shafran |
| 2008/0046122 A1 | 2/2008 | Manzo |
| 2008/0077159 A1 | 3/2008 | Madhani et al. |
| 2008/0097187 A1 | 4/2008 | Gielen et al. |
| 2008/0114340 A1 | 5/2008 | Fox et al. |
| 2008/0123921 A1 | 5/2008 | Gielen et al. |
| 2008/0123922 A1 | 5/2008 | Gielen et al. |
| 2008/0195085 A1 | 8/2008 | Loeb |
| 2008/0208034 A1 | 8/2008 | Yang et al. |
| 2008/0242978 A1 | 10/2008 | Simon et al. |
| 2008/0243142 A1 | 10/2008 | Gildenberg |
| 2008/0243218 A1 | 10/2008 | Bottomley et al. |
| 2008/0255583 A1 | 10/2008 | Gielen et al. |
| 2008/0262584 A1 | 10/2008 | Bottomley et al. |
| 2008/0269588 A1 | 10/2008 | Csavoy et al. |
| 2008/0269602 A1 | 10/2008 | Csavoy et al. |
| 2008/0287917 A1 | 11/2008 | Cunningham |
| 2008/0306375 A1 | 12/2008 | Sayler et al. |
| 2009/0012509 A1 | 1/2009 | Csavoy et al. |
| 2009/0018446 A1 | 1/2009 | Medan et al. |
| 2009/0048588 A1 | 2/2009 | Peng et al. |
| 2009/0048606 A1 | 2/2009 | Tipirneni et al. |
| 2009/0082783 A1 | 3/2009 | Piferi |
| 2009/0088623 A1 | 4/2009 | Vortman et al. |
| 2009/0099045 A1 | 4/2009 | Jackson et al. |
| 2009/0112082 A1 | 4/2009 | Piferi et al. |
| 2009/0118610 A1 | 5/2009 | Karmarkar et al. |
| 2009/0124398 A1 | 5/2009 | Thompson |
| 2009/0131783 A1 | 5/2009 | Jenkins et al. |
| 2009/0148493 A1 | 6/2009 | Ballerstadt et al. |
| 2009/0192487 A1 | 7/2009 | Broaddus et al. |
| 2009/0198309 A1 | 8/2009 | Gowda et al. |
| 2009/0204111 A1 | 8/2009 | Bissig et al. |
| 2009/0234368 A1 | 9/2009 | Gore |
| 2009/0238429 A1 | 9/2009 | Roland et al. |
| 2009/0240242 A1 | 9/2009 | Neuberger |
| 2009/0266760 A1 | 10/2009 | Jackson et al. |
| 2009/0275130 A1 | 11/2009 | Navran et al. |
| 2009/0287199 A1 | 11/2009 | Hanley et al. |
| 2009/0308400 A1 | 12/2009 | Wilson et al. |
| 2009/0326525 A1 | 12/2009 | Hixon et al. |
| 2010/0016930 A1 | 1/2010 | Gowda et al. |
| 2010/0022951 A1 | 1/2010 | Ferrera et al. |
| 2010/0030076 A1 | 2/2010 | Vortman et al. |
| 2010/0041938 A1 | 2/2010 | Stoianovici et al. |
| 2010/0042112 A1 | 2/2010 | Qureshi et al. |
| 2010/0079580 A1 | 4/2010 | Waring, IV |
| 2010/0082035 A1 | 4/2010 | Keefer |
| 2010/0087336 A1 | 4/2010 | Jackson et al. |
| 2010/0146713 A1 | 6/2010 | Medan et al. |
| 2010/0179425 A1 | 7/2010 | Zadicario |
| 2010/0198052 A1 | 8/2010 | Jenkins et al. |
| 2010/0241036 A1 | 9/2010 | Vortman et al. |
| 2010/0305580 A1 | 12/2010 | Henderson et al. |
| 2010/0312094 A1 | 12/2010 | Guttman et al. |
| 2010/0312095 A1 | 12/2010 | Jenkins et al. |
| 2010/0312096 A1 | 12/2010 | Guttman et al. |
| 2010/0318002 A1 | 12/2010 | Prus et al. |
| 2011/0009734 A1 | 1/2011 | Foley et al. |
| 2011/0009828 A1 | 1/2011 | Prechtel et al. |
| 2011/0034800 A1 | 2/2011 | Vitek et al. |
| 2011/0040172 A1 | 2/2011 | Carpentier et al. |
| 2011/0046472 A1 | 2/2011 | Schmidt et al. |
| 2011/0046475 A1 | 2/2011 | Assif et al. |
| 2011/0066032 A1 | 3/2011 | Vitek et al. |
| 2011/0118715 A1 | 5/2011 | Zerfas |
| 2011/0137147 A1 | 6/2011 | Skliar et al. |
| 2011/0141759 A1 | 6/2011 | Smith |

(56) References Cited

U.S. PATENT DOCUMENTS

| | | |
|---|---|---|
| 2011/0166447 A1 | 7/2011 | Windolf et al. |
| 2011/0175615 A1 | 7/2011 | Grissom et al. |
| 2011/0190787 A1 | 8/2011 | Sahni et al. |
| 2011/0217665 A1 | 9/2011 | Walsh et al. |
| 2011/0224576 A1 | 9/2011 | Jackson et al. |
| 2011/0226260 A1 | 9/2011 | Eder et al. |
| 2011/0230753 A1 | 9/2011 | Mahon et al. |
| 2011/0237930 A1 | 9/2011 | Donaldson et al. |
| 2011/0238139 A1 | 9/2011 | Gowda et al. |
| 2011/0251528 A1 | 10/2011 | Canney et al. |
| 2011/0260728 A1 | 10/2011 | Biber et al. |
| 2011/0267059 A1 | 11/2011 | Shvartsberg et al. |
| 2011/0270075 A1 | 11/2011 | Vitek et al. |
| 2011/0270136 A1 | 11/2011 | Vitek et al. |
| 2011/0270366 A1 | 11/2011 | Mahon et al. |
| 2011/0295161 A1 | 12/2011 | Chopra et al. |
| 2011/0301450 A1 | 12/2011 | Hue et al. |
| 2011/0306054 A1 | 12/2011 | Jackson et al. |
| 2011/0319747 A1 | 12/2011 | Schmidt et al. |
| 2011/0319748 A1 | 12/2011 | Bronskill et al. |
| 2011/0319910 A1 | 12/2011 | Roelle et al. |
| 2012/0015359 A1 | 1/2012 | Jackson et al. |
| 2012/0029396 A1 | 2/2012 | Vortman et al. |
| 2012/0053573 A1 | 3/2012 | Alksnis |
| 2012/0059243 A1 | 3/2012 | Vortman et al. |
| 2012/0059335 A1 | 3/2012 | Bobo, Sr. |
| 2012/0070058 A1 | 3/2012 | Raju et al. |
| 2012/0071746 A1 | 3/2012 | Vortman et al. |
| 2012/0095364 A1 | 4/2012 | Bobo, Sr. |
| 2012/0101412 A1 | 4/2012 | Vortman et al. |
| 2012/0108459 A1 | 5/2012 | Jackson et al. |
| 2012/0121533 A1 | 5/2012 | Jackson |
| 2012/0165225 A1 | 6/2012 | Stepanov et al. |
| 2012/0191020 A1 | 7/2012 | Vitek et al. |
| 2012/0197112 A1 | 8/2012 | McNichols |
| 2012/0245573 A1 | 9/2012 | Gowda et al. |
| 2013/0006095 A1 | 1/2013 | Jenkins et al. |
| 2013/0018430 A1 | 1/2013 | Murphy |
| 2013/0030408 A1 | 1/2013 | Piferi et al. |
| 2013/0034915 A1 | 2/2013 | Ballerstadt et al. |
| 2013/0035582 A1 | 2/2013 | Radulescu et al. |
| 2013/0041356 A1 | 2/2013 | Smith et al. |
| 2013/0053678 A1 | 2/2013 | Vitek et al. |
| 2013/0053867 A1 | 2/2013 | Gowda et al. |
| 2013/0060253 A1 | 3/2013 | Couture et al. |
| 2013/0085342 A1 | 4/2013 | Stefanchik et al. |
| 2013/0102883 A1 | 4/2013 | Piferi et al. |
| 2013/0116543 A1 | 5/2013 | Jenkins et al. |
| 2013/0119984 A1 | 5/2013 | Levy et al. |
| 2013/0123598 A1 | 5/2013 | Jenkins et al. |
| 2013/0131496 A1 | 5/2013 | Jenkins et al. |
| 2013/0150704 A1 | 6/2013 | Vitek et al. |
| 2013/0150756 A1 | 6/2013 | Vitek et al. |
| 2013/0157871 A1 | 6/2013 | Jackson |
| 2013/0158577 A1 | 6/2013 | Mahon et al. |
| 2013/0163841 A1 | 6/2013 | Geiger |
| 2013/0184563 A1 | 7/2013 | Driemel et al. |
| 2013/0190607 A1 | 7/2013 | Biber et al. |
| 2013/0217950 A1 | 8/2013 | Partanen et al. |
| 2013/0245243 A1 | 9/2013 | Jackson |
| 2013/0245741 A1 | 9/2013 | Atalar et al. |
| 2013/0274778 A1 | 10/2013 | Mercier et al. |
| 2013/0325012 A1 | 12/2013 | Piferi et al. |
| 2014/0024909 A1 | 1/2014 | Vij et al. |
| 2014/0024925 A1 | 1/2014 | Piferi |
| 2014/0024927 A1 | 1/2014 | Piferi |
| 2014/0034377 A1 | 2/2014 | Vij |
| 2014/0046167 A1 | 2/2014 | Vij et al. |
| 2014/0046343 A1 | 2/2014 | Okazaki et al. |
| 2014/0066750 A1 | 3/2014 | Piferi et al. |
| 2014/0066953 A1 | 3/2014 | Keating et al. |
| 2014/0112095 A1 | 4/2014 | Medan et al. |
| 2015/0209599 A1 | 7/2015 | Schlosser et al. |

FOREIGN PATENT DOCUMENTS

| | | |
|---|---|---|
| CA | 2398967 A1 | 8/2001 |
| CA | 2403822 A1 | 10/2001 |
| CA | 2404352 A1 | 10/2001 |
| CA | 2482291 A1 | 10/2002 |
| CA | 2587691 A1 | 5/2006 |
| CA | 2606824 A1 | 11/2006 |
| CA | 2623453 A1 | 4/2007 |
| CA | 2679498 A1 | 9/2008 |
| CA | 2681367 A1 | 9/2008 |
| CA | 2695494 A1 | 12/2008 |
| CA | 2700523 A1 | 4/2009 |
| CA | 2700529 A1 | 4/2009 |
| CA | 2700531 A1 | 4/2009 |
| CA | 2700577 A1 | 4/2009 |
| CA | 2700607 A1 | 4/2009 |
| CA | 2704739 A1 | 4/2009 |
| CA | 2252431 C | 7/2009 |
| CA | 2648973 C | 7/2009 |
| CA | 2715015 A1 | 9/2009 |
| CA | 2748053 A1 | 4/2010 |
| CA | 2753397 A1 | 9/2010 |
| CA | 2372001 C | 10/2010 |
| CA | 2764677 A1 | 12/2010 |
| CA | 1317641 | 5/2011 |
| CA | 2487140 C | 9/2011 |
| CA | 2800238 A1 | 9/2011 |
| CA | 2482202 C | 7/2012 |
| CA | 2849106 A1 | 4/2013 |
| CA | 2575313 C | 7/2013 |
| CA | 2548226 C | 1/2014 |
| CN | 2620289 Y | 6/2004 |
| CN | 2748071 Y | 12/2005 |
| CN | 101040772 A | 9/2007 |
| CN | 101194853 A | 6/2008 |
| DE | 26 21 909 A1 | 12/1977 |
| EP | 0 610 991 A2 | 8/1994 |
| EP | 0 614 651 A1 | 9/1994 |
| EP | 0 755 697 A2 | 1/1997 |
| EP | 1 046 377 A2 | 10/2000 |
| EP | 0 844 581 B1 | 7/2007 |
| EP | 1 829 764 | 9/2007 |
| EP | 1 455 672 B1 | 5/2008 |
| EP | 1 985 330 A1 | 10/2008 |
| JP | 54-88120 | 7/1979 |
| JP | 59-42165 | 3/1984 |
| JP | 60-154698 | 8/1985 |
| JP | 7-308393 | 11/1995 |
| JP | 7-328028 | 12/1995 |
| JP | 9-038220 | 2/1997 |
| JP | 10-155805 | 6/1998 |
| JP | 10-258066 | 9/1998 |
| JP | 11-253562 | 9/1999 |
| JP | 2000-000319 | 1/2000 |
| JP | 2000-126316 | 5/2000 |
| JP | 2002-543865 | 12/2002 |
| WO | WO 90/05494 | 5/1990 |
| WO | WO 1992/010142 | 6/1992 |
| WO | WO 93/20769 | 10/1993 |
| WO | WO 94/04220 | 3/1994 |
| WO | WO 1994/023308 | 10/1994 |
| WO | WO 95/29737 | 11/1995 |
| WO | WO 1997/040396 | 10/1997 |
| WO | WO 98/23214 | 6/1998 |
| WO | WO 98/51229 | 11/1998 |
| WO | WO 98/52465 | 11/1998 |
| WO | WO 99/51156 | 10/1999 |
| WO | WO 00/23000 | 4/2000 |
| WO | WO 2000/028895 | 5/2000 |
| WO | WO 2000/032102 | 6/2000 |
| WO | WO 2000/062672 | 10/2000 |
| WO | WO 2000/064003 | 10/2000 |
| WO | WO 00/67640 | 11/2000 |
| WO | WO 2001/006925 | 2/2001 |
| WO | WO 2001/025810 | 4/2001 |
| WO | WO 2001/035825 | 5/2001 |
| WO | WO 2001/040819 | 6/2001 |
| WO | WO 2001/056469 | 8/2001 |

(56) References Cited

FOREIGN PATENT DOCUMENTS

| | | |
|---|---|---|
| WO | WO 2001/065490 | 9/2001 |
| WO | WO 01/076498 A3 | 10/2001 |
| WO | WO 2001/073461 | 10/2001 |
| WO | WO 2001/074241 | 10/2001 |
| WO | WO 2001/080708 | 11/2001 |
| WO | WO 2001/080709 | 11/2001 |
| WO | WO 2001/082806 | 11/2001 |
| WO | WO 2002/000093 | 1/2002 |
| WO | WO 2002/000298 | 1/2002 |
| WO | WO 2002/009812 | 2/2002 |
| WO | WO 2002/024075 | 3/2002 |
| WO | WO 2002/024094 | 3/2002 |
| WO | WO 2002/043804 | 6/2002 |
| WO | WO 2002/043805 | 6/2002 |
| WO | WO 2002/044753 | 6/2002 |
| WO | WO 2002/045073 | 6/2002 |
| WO | WO 2002/051501 | 7/2002 |
| WO | WO 2002/058791 | 8/2002 |
| WO | WO 2002/083016 | 10/2002 |
| WO | WO 2002/084316 | 10/2002 |
| WO | WO 2002/085216 | 10/2002 |
| WO | WO 2002/097466 | 12/2002 |
| WO | WO 2002/103380 | 12/2002 |
| WO | WO 2003/011160 | 2/2003 |
| WO | WO 2003/017843 | 3/2003 |
| WO | WO 2003/042707 | 5/2003 |
| WO | WO 2003/048702 | 6/2003 |
| WO | WO 2003/052444 | 6/2003 |
| WO | WO 03/094759 A1 | 11/2003 |
| WO | WO 2003/097162 | 11/2003 |
| WO | WO 2003/102614 | 12/2003 |
| WO | WO 2004/056421 | 7/2004 |
| WO | WO 2004/075722 A2 | 9/2004 |
| WO | WO 2004/103472 | 12/2004 |
| WO | WO 2004/105624 | 12/2004 |
| WO | WO 2005/046451 A2 | 5/2005 |
| WO | WO 2005/046753 | 5/2005 |
| WO | WO 2006/014966 | 2/2006 |
| WO | WO 2006/018686 | 2/2006 |
| WO | WO 2006/021851 | 3/2006 |
| WO | WO 2006/055554 | 5/2006 |
| WO | WO 2006/119492 | 11/2006 |
| WO | WO 2006/136912 | 12/2006 |
| WO | WO 2007/047966 | 4/2007 |
| WO | WO 2007/056458 A2 | 5/2007 |
| WO | WO 2007/060474 A1 | 5/2007 |
| WO | WO 2007/064937 | 6/2007 |
| WO | WO 2007/085892 | 8/2007 |
| WO | WO 2007/129166 | 11/2007 |
| WO | WO 2008/015520 | 2/2008 |
| WO | WO 2008/015521 | 2/2008 |
| WO | WO 2008/015522 | 2/2008 |
| WO | WO 2008/015523 | 2/2008 |
| WO | WO 2008/070685 | 6/2008 |
| WO | WO 2008/109864 | 9/2008 |
| WO | WO 2008/115383 | 9/2008 |
| WO | WO 2008/115426 | 9/2008 |
| WO | WO 2008/153975 | 12/2008 |
| WO | WO 2009/007847 | 1/2009 |
| WO | WO 2009/042130 | 4/2009 |
| WO | WO 2009/042131 | 4/2009 |
| WO | WO 2009/042135 | 4/2009 |
| WO | WO 2009/042136 | 4/2009 |
| WO | WO 2009/042152 | 4/2009 |
| WO | WO 2009/042155 | 4/2009 |
| WO | WO 2009/042160 | 4/2009 |
| WO | WO 2009/044276 | 4/2009 |
| WO | WO 2009/067205 | 5/2009 |
| WO | WO 2009/117069 | 9/2009 |
| WO | WO 2009/124301 | 10/2009 |
| WO | WO 2009/135198 | 11/2009 |
| WO | WO 2010/030373 | 3/2010 |
| WO | WO 2010/034099 | 4/2010 |
| WO | WO 2010/058292 | 5/2010 |
| WO | WO 2010/058293 | 5/2010 |
| WO | WO 2010/082135 | 7/2010 |
| WO | WO 2010/087961 | 8/2010 |
| WO | WO 2010/110929 | 9/2010 |
| WO | WO 2010/119340 | 10/2010 |
| WO | WO 2010/141102 | 12/2010 |
| WO | WO 2010/143072 | 12/2010 |
| WO | WO 2010/144402 | 12/2010 |
| WO | WO 2010/144405 | 12/2010 |
| WO | WO 2010/144419 | 12/2010 |
| WO | WO 2010/148083 | 12/2010 |
| WO | WO 2010/148088 | 12/2010 |
| WO | WO 2011/013001 | 2/2011 |
| WO | WO 2011/015949 | 2/2011 |
| WO | WO 2011/021106 | 2/2011 |
| WO | WO 2011/024074 | 3/2011 |
| WO | WO 2011/028505 | 3/2011 |
| WO | WO 2011/045669 | 4/2011 |
| WO | WO 2011/058437 | 5/2011 |
| WO | WO 2011/087495 | 7/2011 |
| WO | WO 2011/090990 | 7/2011 |
| WO | WO 2011/112249 | 9/2011 |
| WO | WO 2011/112251 | 9/2011 |
| WO | WO 2011/115664 | 9/2011 |
| WO | WO 2011/130107 | 10/2011 |
| WO | WO 2011/135455 | 11/2011 |
| WO | WO 2011/135458 | 11/2011 |
| WO | WO 2012/014074 | 2/2012 |
| WO | WO 2012/038826 | 3/2012 |
| WO | WO 2012/052847 | 4/2012 |
| WO | WO 2012/112829 | 8/2012 |
| WO | WO 2012/116265 | 8/2012 |
| WO | WO2013063027 A1 | 10/2012 |
| WO | WO 2012/147614 A1 | 11/2012 |
| WO | WO 2012/154961 | 11/2012 |
| WO | WO 2013/028811 | 2/2013 |
| WO | WO 2013/030671 | 3/2013 |
| WO | WO 2013/049108 | 4/2013 |
| WO | WO 2013/117991 | 8/2013 |
| WO | WO 2013/117992 | 8/2013 |
| WO | WO 2013/181008 | 12/2013 |
| WO | WO 2014/003855 A1 | 1/2014 |
| WO | WO 2014/014585 | 1/2014 |
| WO | WO 2014/039481 | 3/2014 |

OTHER PUBLICATIONS

U.S. Office Action dated Jun. 27, 2016 in U.S. Appl. No. 14/661,310, filed Mar. 18, 2015.
Lubowitz, "Thermal chondroplasty using the Smith & Nephew Dyonics Glider Articular Cartilage Probe," https://www.smith-nephew.com/global/surgicaltechniques/sports%20med/dyonics~lider_pre-shaped_probe_tg_10600072a.pdf , Jul. 2006, pp. 1-8.
Office Action dated Jan. 12, 2016 in Japanese Patent Application No. 2014-503267 (with English language translation).
International Search Report dated Jul. 27, 2015 in PCT/US2015/021228 filed Mar. 18, 2015.
Written Opinion dated Jul. 27, 2015 in PCT/US2015/021228 filed Mar. 18, 2015.
International Search Report and Written Opinion dated Jun. 10, 2013, in PCT/US13/32273.
Office Action dated Dec. 27, 2013, in Israeli Patent Application No. 210878.
International Preliminary Report on Patentability dated Feb. 15, 2011, in PCT/CA2009/01137, 8 pages.
International Preliminary Report on Patentability dated Feb. 15, 2011, in PCT/CA2009/001138, 5 pages.
Office Action dated Oct. 25, 2011, in Brazilian Patent Application No. PI-0214951-6 (English translation).
Office Action dated May 28, 2013, in Brazilian Patent Application No. PI-0214951-6 (English translation).
Office Action dated Nov. 1, 2012, in Japanese Patent Application No. 2011-522361 (with English-language translation).
Combined Chinese OA and Search Report dated Mar. 13, 2013, in Chinese Patent Application No. 200980131609.X.
Kahn et al., "MRI-Guided Laser-Induced Interstitial Thermotherapy of Cerebral Neoplasms," Journal of Computer Assisted Tomogra-

(56) References Cited

OTHER PUBLICATIONS phy, vol. 18, No. 4, pp. 519-532, Jul./Aug. 1994, Raven Press, Ltd., New York, NY.

Kahn et al., "In Vivo MRI Thermometry Using a Phase-Sensitive Sequence: Preliminary Experience During MRI-Guided Laser-Induced Interstitial Thermotherapy of Brain Tumors," Journal of Magnetic Resonance Imaging, vol. 8, No. 1, pp. 160-164, Williams & Wilkins, 1998, Baltimore, MD.

Vogl et al., "Internally Cooled Power Laser for MR-guided Interstitial Laser-induced Thermotherapy of Liver Lesions: Initial Clinical Results", in Radiology, 1998, 209: pp. 381-385.

McNichols et al., "MR Thermometry-Based Feedback Control of Laser Interstitial Thermal Therapy at 980 nm," Lasers in Surgery and Medicine, 2004, 34: 48-55, Wiley-Liss, Inc.

Schwarzmaier et al., "MR-guided laser-induced interstitial thermotherapy of recurrent glioblastoma multiforme: Preliminary results in 16 patients," European Journal of Radiology, vol. 59, Issue 2, pp. 208-215, Aug. 2006.

Office Action dated Oct. 8, 2012, in Chinese Patent Application No. 200980131600.9 (with English-language translation).

Office Action dated Jul. 17, 2013, in Japanese Patent Application No. 2011-522361 (with English-language translation).

Office Action dated Jul. 29, 2013, in Japanese Patent Application No. 2011-522360 (with English-language translation).

Jerome Shaunnessey, Petition for General Supervisory Review by the Director under 37 CFR 1.181, Jul. 2014, 6 pages.

International Search Report dated Aug. 3, 2012 in PCT/IB2012/051716.

Office Action dated Nov. 1, 2012, in Japanese Patent Application No. 2011-522360 (with English Translation).

Supplementary European Search Report dated Oct. 18, 2013, in European Patent Application No. 09806277.1.

Castro et al. "Interstitial laaser phototherapy assisted by magnetic resonance imaging: A new technique for monitoring laser-tissue interaction" The Laryngoscope, vol. 100, Issue , pp. 541-547, May 1990 (abstract only).

Nabavi et al. "Neurosurgical procedures in a 0.5 tesla, open-configuration intraoperative MRI: planning, visualization, and navigation" Automedica, vol. 00, pp. 1-35, 2001.

T. Menovsky, et al., "Interstitial Laser Thermotherapy in Neurosurgery: A Review", Acta Neurochir (Wien) (1996) 138:1019-1026, 8 pages.

Ferenc A. Jolesz M.D., et al., "MRI-Guided Laser-Induced Interstitial Thermotherapy: Basic Principles", Harvard Medical School and Brigham and Women's Hospital, Department of Radiology, appears in: SPIE Institute on Laser-Induced Interstitial Thermotherapy (LITT), Jun. 22-23, 1995, 17 pages.

Thorsten Harth, et al., "Determination of Laser-Induced Temperature Distributions Using Echo-Shifted TurboFLASH", MRM 38:238-245 (1997), 8 pages.

Lawrence P. Panych, et al., "Effects Related to Temperature Changes during MR Imaging", JMRI, vol. 2, No. 1, Jan./Feb. 1992, pp. 69-74.

John De Poorter, "Noninvasive MRI Thermometry with the Proton Resonance Frequency Method: Study of Susceptibility Effects", MRM 34:359-367 (1995), 9 pages.

Ron Corbett, et al., "Noninvasive Measurements of Human Brain Temperature Using Volume-Localized Proton Magnetic Resonance Spectroscopy", Journal of Cerebral Blood Flow and Metabolism, vol. 17, No. 4, 1997, pp. 363-369.

Waldemar Wlodarczyk, et al., "Comparison of four magnetic resonance methods for mapping small temperature changes", Phys. Med. Biol. 44, 1999, pp. 607-624.

Carpentier, et al. "Real-Time Magnetic Resonance-Guided Laser Thermal Therapy for Focal Metastatic Brain Tumors", Operative Neurogurgery 1, vol. 63, 2008, pp. 21-39.

Canney, et al. "A Multi-element Interstitial Ultrasound Applicator for the Thermal Therapy of Brain Tumors", Acoustical Society of America, Pt. 2, Aug. 2013, pp. 1647-1655.

Carpentier, et al. "MR-Guided Laser Induced Thermal Therapy (LITT) for Recurrent Glioblastomas", Lasers in Surgery and Medicine, vol. 44, pp. 361-368, 2012.

Carpentier, et al. "Laser Thermal Therapy: Real-time MRI-guided and Computer-controlled Procedures for Metastatic Brain Tumors", Lasers in Surgery and Medicine, vol. 43, pp. 943-950, 2011.

Gewiese, et al. "Magenetic Resonance Imaging-Controlled Laser-Induced Interstitial Thermotherapy", Investigative Radiology, vol. 29, No. 3, pp. 345-351, 1994.

Ferenc A. Jolesz, MD, et al., "MR Imaging of Laser-Tissue Interactions", Magnetic Resonance Imaging, Radiology 1988; 168, pp. 249-253.

Yoshimi Anzai, MD, et al., "Nd:YAg Interstitial Laser Phototherapy Guided by Magnetic Resonance Imaging in an Ex Vivo Model: Dosimetry of Laser-Mr-Tissue Interaction", Laryngoscope 101: Jul. 1991, pp. 755-760.

Harvey E. Cline, et al., "MR-Guided Focused Ultrasound Surgery", Journal of Computer Assisted Tomography, Nov./Dec. 1992, vol. 16, No. 6, pp. 956-965.

Harvey E. Cline, PhD, et al., "Focused US System for MR Imaging-guided Tumor Ablation" Magnetic Resonance Imaging, Radiology 1995; Mar. 1995, vol. 194, No. 3, pp. 731-737.

Kullervo Hynynen, PhD, et al, "A Clinical, Noninvasive, MR Imaging-monitored Ultrasound Surgery Method", Imaging & Therapeutic Technology, RadioGraphics 1996; Janunary 1996, vol. 16, No. 1, pp. 185-195.

Nobuhiko Hata, et al., "Computer-Assisted Intra-Operative Magnetic Resonance Imaging Monitoring of Interstitial Laser Therapy in the Brain: A Case Report", Journal of Biomedical Optics, Jul. 1998, vol. 3, No. 3, pp. 304-311.

Joachim Kettenbach, MD, et al., "Monitoring and Visualization Techniques for MR-Guided Laser Ablations in an Open MR System" Journal of Magnetic Resonance Imaging, Jul./Aug. 1998, vol. 8, No. 4, pp. 933-943.

Ferenc A. Jolesz, MD, et al., "Integration of Interventional MRI with Computer-Assisted Surgery", Journal of Magnetic Resonance Imaging, Jan. 2001;13(1), pp. 69-77.

Frederic C. Vimeux, et al., "Real-Time Control of Focused Ultrasound Heating Based on Rapid MR Thermometry", Investigative Radiology, Mar. 1999, vol. 34(3), pp. 190-193.

J. Delannoy, et al., "Hyperthermia system combined with a magnetic resonance imaging unit", Medical Physics, vol. 17, No. 5, Sep./Oct. 1990, pp. 855-860.

Zientara, Gary P., et al. "MRI monitoring of laser ablation using optical flow." Journal of Magnetic Resonance Imaging 8.6 (1998): 1306-1318.

Alan R. Bleier, et al., "Real-Time Magnetic Resonance Imaging of Laser Heat Deposition in Tissue", Magnetic Resonance in Medicine 21, 1991, pp. 132-137.

Kullervo Hynynen, et al., "Focused Ultrasound Thermal Surgery Guided and Monitored by Magnetic Resonance Imaging", Interventional Radiology, 1997, vol. 2, Third Edition, pp. 1811-1816 (with cover pages).

Ferenc A. Jolesz, "MR-guided thermal ablation of brain tumors", Interventional MR: Techniques and Clinical Experience, 1998, pp. 123-129 (with cover pages).

F.A. Jolesz, et al., "Image-Guided Neurosurgery with Intraoperative MRI", Interventional Magnetic Resonance Imaging, 1998, pp. 253-260 (with cover pages).

Kullervo Hynynen, et al., "Principles of MR-Guided Focused Ultrasound", Chapter 25, Interventional MRI, 1999, pp. 237-243 (with cover pages).

Masoud Panjehpour, PhD et al., "Nd:YAg Laser-Induced Interstitial Hyperthermia Using a Long Frosted Contact Probe", Lasers in Surgery and Medicine 10, 1990, pp. 16-24.

S. Bosman, et al., "Effect of percutaneous interstitial thermal laser on normal liver of pigs: sonographic and histopathological correlations", Br. J. Surg., May 1991, vol. 78, No. 5, pp. 572-575.

M. Fan, M.D., et al., "Interstitial 1.06 Nd:YAg Laser Thermotherapy for Brain Tumors Under Real-Time Monitoring of MRI: Experimental Study and Phase I Clinical Trial", Journal of Clinical Laser Medicine & Surgery, vol. 10, No. 5, 1992, pp. 355-361.

(56) References Cited

OTHER PUBLICATIONS

Office Action issued in Chinese Patent Application No. 200980131609.X dated Jan. 10, 2014.
Office Action dated Aug. 22, 2013, in Chinese Patent Application No. 200980131600.9 (with English-language translation).
Vogl et al. "Internally Cooled Power Laser for MR-guided Interstitial Laser-induced Thermotherapy of Liver Lesions: Initial Clinical Results," Radiology, vol. 209, No. 2. 1998, 381-385.
Office Action dated Jan. 6, 2016 in Japanese Patent Application No. 2014-503267 with English Translation.

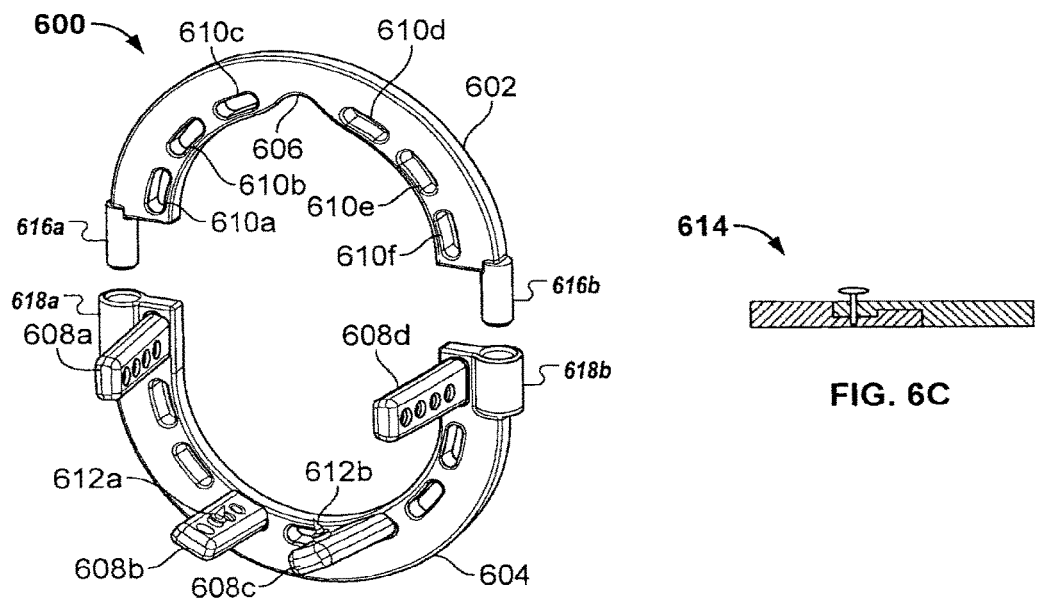
FIG. 6A
FIG. 6C
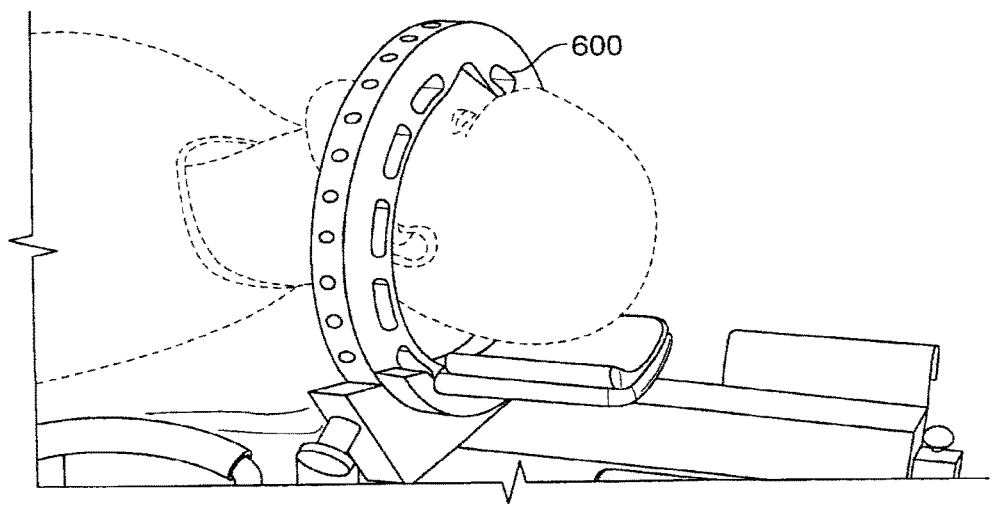
FIG. 6B

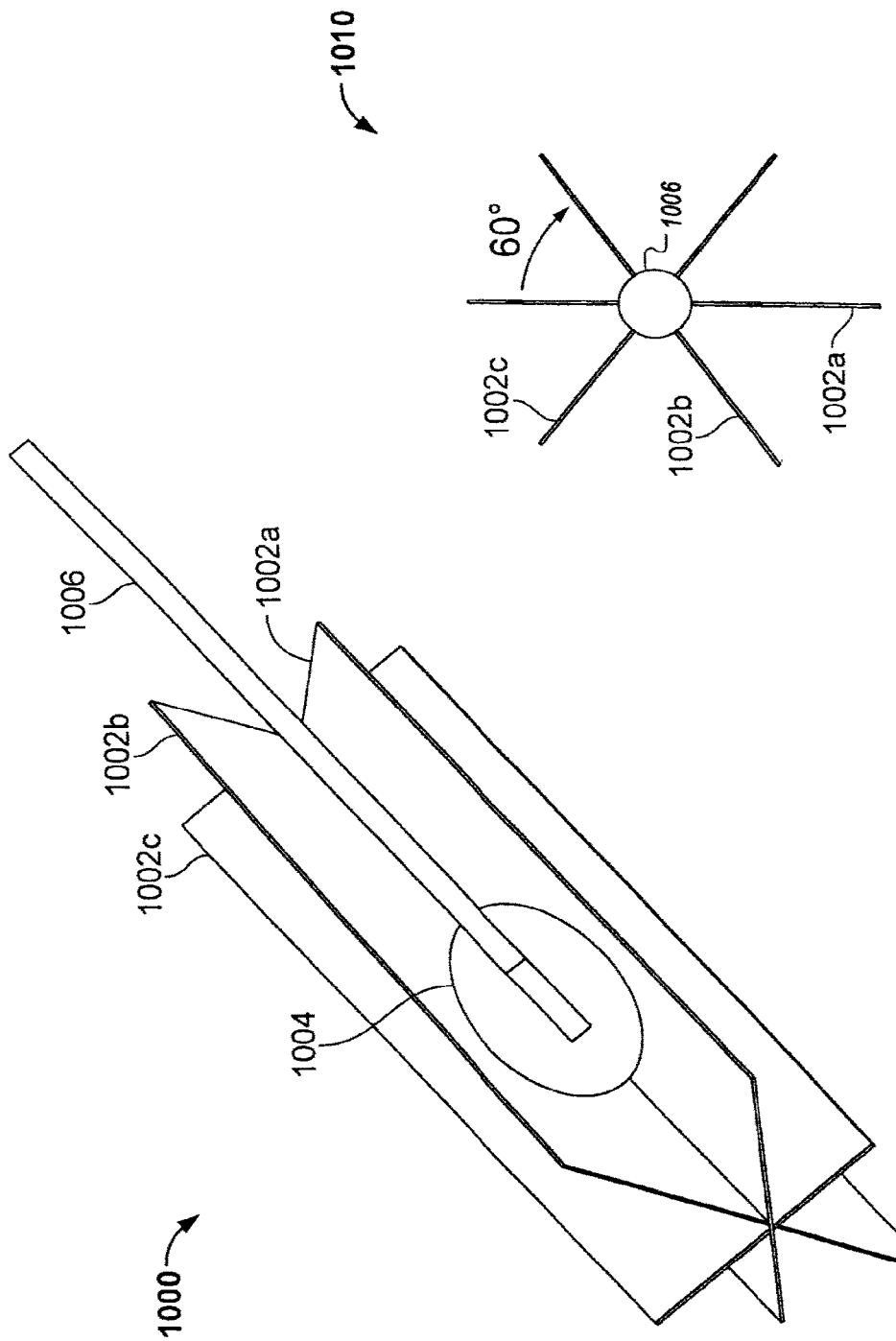

IMAGE-GUIDED THERAPY OF A TISSUE

RELATED APPLICATIONS

The present application is a continuation of U.S. Non Provisional patent application Ser. No. 14/661,138 filed Mar. 18, 2015. application Ser. No. 14/661,138 is related to and claims the benefit of U.S. Provisional Patent Application 61/955,124 entitled "Image-Guided Therapy of a Tissue" and filed Mar. 18, 2014. The contents of each of the above listed applications are hereby incorporated by reference in their entireties.

BACKGROUND

Cancerous brain tumors can be "primary" tumors, meaning that the tumors originate in the brain. Primary tumors include brain tissue with mutated DNA that grows (sometimes aggressively) and displaces or replaces healthy brain tissue. Gliomas are one type of primary tumor that indicate cancer of the glial cells of the brain. While primary tumors can appear as single masses, they can often be quite large, irregularly-shaped, multi-lobed and/or infiltrated into surrounding brain tissue.

Primary tumors may not be diagnosed until the patient experiences symptoms, including those such as headaches, altered behavior, and sensory impairment. However, by the time the symptoms develop, the tumor may already be large and aggressive.

One treatment for cancerous brain tumors is surgery. Surgery involves a craniotomy (i.e., removal of a portion of the skull), dissection, and total or partial tumor resection. The objectives of surgery may include removing or lessening of the number of active malignant cells within the brain, or reducing a patient's pain or functional impairment due to the effect of the tumor on adjacent brain structures. Not only can surgery be invasive and accompanied by risks, for some tumors, surgery is often only partially effective. In other tumors, surgery may not be feasible. Surgery may risk impairment to the patient, may not be well-tolerated by the patient, and/or may involve significant costs, recovery time, and recovery efforts.

Another treatment for cancerous brain tumors is stereotactic radiosurgery (SRS). SRS is a treatment method by which multiple intersecting beams of radiation are directed at the tumor such that, at the point of intersection of the beams, a lethal dose of radiation is delivered, while tissue in the path of any single beam remains unharmed. However, confirmation that the tumor has been killed is often not possible for several months post-treatment. Furthermore, in situations where high doses of radiation may be required to kill a tumor, such as in the case of multiple or recurring tumors, it is common for the patient to reach a toxic threshold for radiation dose, prior to killing all of the tumors. Reaching this toxic threshold renders further radiation is inadvisable.

SUMMARY

In one aspect, the present disclosure relates to a head fixation apparatus including a number of support posts, a curved ring portion including a number of connectors configured to adjustably and releasably mount the number of support posts on the lower ring portion, such that the number of support posts are selectively mounted to a subset of the number of connectors in a customized arrangement for a patient, and a ring mount configured for fixation to a platform. The ring mount may include a curved channel substantially matching a curvature of the curved ring portion, and a mount locking mechanism for locking the curved ring portion within the channel of the ring mount. The number of support posts may be configured to support the head of the patient. The curved ring portion may be configured to rotate within the channel of the ring mount while the ring mount is fixed to the platform, an angular head position of the patient being selectably adjustable while the patient is laying on the platform. The mount locking mechanism may be configured to lockably engage the curved ring portion within the channel of the ring mount upon positioning of the angular head position of the patient.

In some embodiments, the curved ring portion and the ring mount channel are semicircular.

The head fixation apparatus may include an upper ring portion including an upper locking mechanism, where the curved ring portion includes a lower locking mechanism configured to mate with the upper locking mechanism such that the upper ring portion and the lower ring portion encircle the head of the patient. The upper ring portion may include a nose indent in which a nose of the patient aligns when the head of the patient is positioned in the head fixation apparatus. The lower locking mechanism may be configured to engage with the upper locking mechanism at two or more mating positions, where an interior area of a resulting head fixation ring is adjustable. One of the upper locking mechanism and the lower locking mechanism may include a number of openings, and the other of the upper locking mechanism and the lower locking mechanism may include a set screw. One of the upper locking mechanism and the lower locking mechanism may include a number of indents, and the other of the upper locking mechanism and the lower locking mechanism may include a spring-loaded plunger. The head fixation apparatus may further include at least one additional upper ring portion, where one of the upper ring portion and the additional upper ring portion is selected based on a size of the head of the patient. The upper ring portion may include a number of upper support posts, where each support post of the number of upper support posts includes a respective fixation mechanism configured to fix a position of the head of the patient.

In some embodiments, each support post of the number of support posts includes at least one connection point that releasably connects to a respective fixation mechanism that fixes a position of the head of the patient. The respective fixation mechanism may be one of a conforming abutment and a fixation pin. Each support post of the number of support posts may include a number of connection points, where positioning of the respective fixation mechanism upon the respective support post is adjustable. The respective number of connection points may be positioned upon each support post of the number of support posts in an arrangement providing at least one of a) a number of linear connection options and b) a number of radial connection options for connecting the fixation mechanism to the respective support post.

In some embodiments, the mount locking mechanism includes a clamp, and the angular head rotation is continuously adjustable by rotating the curved ring portion within the channel to a desired angular head rotation. The curved ring portion may include a number of mating features for mating with the mount locking mechanism.

In one aspect, the present disclosure relates to a head fixation system for immobilizing a head of a patient, including a number of support posts, where each support post of the number of support posts includes a number of connection points for releasable connection of a respective fixation mechanism to fix a position of the head of the patient, such that positioning of the respective fixation mechanism upon the respective support post is adjustable. The head fixation system may include a curved ring portion including a number of connectors configured to adjustably and releasably mount the number of support posts on the lower ring portion, such that the number of support posts are selectively mounted to a subset of the number of connectors in a customized arrangement for a patient, where the number of support posts are configured, upon mounting to the curved ring portion, to support the head of the patient.

In some embodiments, the head fixation system further includes a ring mount configured for fixation to a platform, where the ring mount includes a curved channel substantially matching a curvature of the curved ring portion, and a mount locking mechanism for locking the curved ring portion within the channel of the ring mount. The curved ring portion may be configured to rotate within the channel of the ring mount while the ring mount is fixed to the platform, an angular head position of the patient being selectably adjustable while the patient is laying on the platform. The mount locking mechanism may be configured to lockably engage the curved ring portion within the channel of the ring mount upon positioning of the angular head position of the patient.

In some embodiments, at least one of the curved ring portion and an upper ring portion is configured to releasably mate with the curved ring portion to encircle the head of the patient. At least one of the curved ring portion and an upper ring portion may include at least one fiducial marker, such that, upon positioning the angular head position of the patient and lockably engaging the curved ring portion with the mount locking mechanism, the at least one fiducial marker identifies an angular head positioning within the channel of the ring mount.

In some embodiments, the head fixation system further includes a memory having instructions stored thereon, where the instructions, when executed, cause a processor to identify, within one or more images, the at least one fiducial marker, and calculate, based upon a position of the at least one fiducial marker, the angle of rotation of the head fixation system. The one or more images may include magnetic resonance (MR) images. The instructions, when executed, may cause the processor to present a model, based upon the calculated angle of rotation, of a patient positioning relative to a neurosurgical apparatus upon a graphical user interface.

The foregoing general description of the illustrative implementations and the following detailed description thereof are merely example aspects of the teachings of this disclosure, and are not restrictive.

BRIEF DESCRIPTION OF THE DRAWINGS

FIGS. 6A and 6B illustrate a head fixation system;

FIG. 6C illustrates a locking mechanism;

FIGS. 10A and 10B illustrate a method for MR thermal monitoring using offset thermal imaging planes.

DETAILED DESCRIPTION OF THE ILLUSTRATIVE EMBODIMENTS

Figure 1:
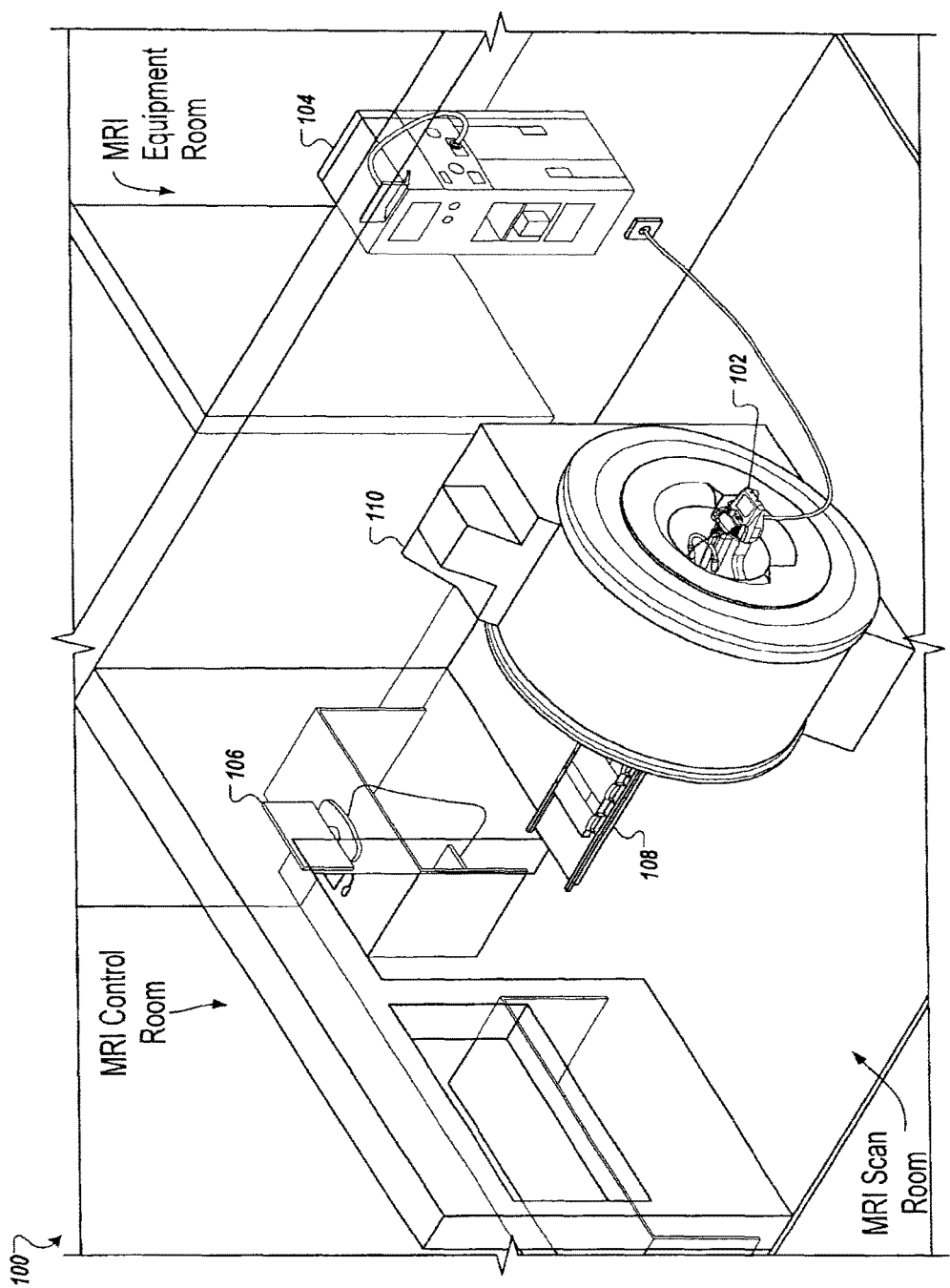
FIG. 1 is an illustration of an exemplary layout of an MRI Control Room, an MRI Scan Room, and an MRI Equipment Room.

In the drawings, like reference numerals designate identical or corresponding parts throughout the several views.

As used herein, the words "a," "an" and the like generally carry a meaning of "one or more," unless stated otherwise. The term "plurality", as used herein, is defined as two or more than two. The term "another", as used herein, is defined as at least a second or more. The terms "including" and/or "having", as used herein, are defined as comprising (i.e., open language). The term "program" or "computer program" or similar terms, as used herein, is defined as a sequence of instructions designed for execution on a computer system. A "program", or "computer program", may include a subroutine, a program module, a script, a function, a procedure, an object method, an object implementation, in an executable application, an applet, a servlet, a source code, an object code, a shared library/dynamic load library and/or other sequence of instructions designed for execution on a computer system.

Reference throughout this document to "one embodiment", "certain embodiments", "an embodiment", "an implementation", "an example" or similar terms means that a particular feature, structure, or characteristic described in connection with the example is included in at least one example of the present disclosure. Thus, the appearances of such phrases or in various places throughout this specification are not necessarily all referring to the same example. Furthermore, the particular features, structures, or characteristics may be combined in any suitable manner in one or more examples without limitation.

The term "or" as used herein is to be interpreted as an inclusive or meaning any one or any combination. Therefore, "A, B or C" means "any of the following: A; B; C; A and B; A and C; B and C; A, B and C". An exception to this definition will occur only when a combination of elements, functions, steps or acts are in some way inherently mutually exclusive.

Further, in individual drawings figures, some components/features shown are drawn to scale to exemplify a particular implementation. For some drawings, components/features are drawn to scale across separate drawing figures. However, for other drawings, components/features are shown magnified with respect to one or more other drawings. Measurements and ranges described herein relate to example embodiments and identify a value or values within a range of 1%, 2%, 3%, 4%, 5%, or, preferably, 1.5% of the specified value(s) in various implementations.

The system or method may include one or more processors and circuits that embody various aspects of various functions by executing corresponding code, instructions and/or software stored on tangible memories or other storage products. A display may include various flat-panel displays, including liquid crystal displays.

The treatment of tumors by heat is referred to as hyperthermia or thermal therapy. Above approximately 57° C., heat energy needs only to be applied for a short period of time since living tissue is almost immediately and irreparably damaged and killed, for example through a process called coagulation, necrosis, or ablation. Malignant tumors, because of their high vascularization and altered DNA, are more susceptible to heat-induced damage than healthy tissue. In other procedures, heat energy is applied to produce reversible cell damage. Temporary damage to cellular structures may cause the cells to be more conducive to certain therapies including, in some examples, radiation therapy and chemotherapy. Different types of energy sources, for example, laser, microwave, radiofrequency, electric, and ultrasound sources may be selected for heat treatment based on factors including: the type of tissue that is being treated, the region of the body in which the tissue to be treated is located, whether cellular death or reversible cellular damage is desired, the nature of energy application parameters for each source, and variability of the energy application parameters. Depending on these factors, the energy source may be extracorporeal (i.e., outside the body), extrastitial (i.e., outside the tumor), or interstitial (i.e., inside the tumor).

In interstitial thermal therapy (ITT), a tumor is heated and destroyed from within the tumor itself, energy may be applied directly to the tumor instead of requiring an indirect route through surrounding healthy tissue. In ITT, energy deposition can be extended throughout the entire tumor. The energy can be applied to heat tissue in the treatment area to a temperature within a range of about 45° to 60° C.

An exemplary ITT process begins by inserting an ultrasound applicator including one or more transducers into the tumor. The ultrasonic energy from the applicator may therefore extend into the tissue surrounding the end or tip including the one or more transducers to effect heating within the tumor. In some implementations, the transducer(s) is/are aligned with an edge of the applicator and the applicator is rotatable so as to rotate the ultrasonic energy beam around the axis of the applicator to effect heating of different parts of the tumor at positions around the applicator. In other implementations or for other applications, the transducer(s) are presented on a tip of the applicator or otherwise surrounding an inserted portion of the applicator. Depending upon the distribution of transducers, the applicator may be moved longitudinally and/or rotated to effect heating of the tumor over a full volume of the targeted region.

In yet other implementations, the ultrasonic applicator is controlled and manipulated by a surgeon with little or no guidance apart from the surgeon's memory of the anatomy of the patient and the location of the tumor. In still other implementations, images may be used during the ITT process to provide guidance for treatment. For example, locations of tumors and other lesions to be excised can be determined using a magnetic resonance imaging (MRI) system or computer tomography (CT) imaging system. During the ITT process, for example, MRI imaging can be used in real time to control or aid in guidance accuracy in an automated or semi-automated fashion.

In some implementations, thermography (e.g., MR thermography, ultrasonic thermography, etc.) provides contemporaneous temperature feedback regarding one or both of the targeted region and the surrounding tissue during the ITT process. The temperature information, for example, can be used to monitor necrosis of tumor tissue while ensuring that surrounding (healthy) tissue suffers minimal to no damage. The temperature feedback, in some implementations, is used to perform either or both of: automating engagement of the ultrasonic energy and cooling functionality of the ultrasonic applicator. In this manner, it is possible to control a temperature distribution or thermal dose in and around the tumor.

Effecting treatment to a tissue, in some implementations, includes an automated drive mechanism with a holder to hold a treatment device (e.g., medical probe, ultrasonic applicator, laser fiber, etc.). In some implementations, the drive mechanism is motorless and consists of thermal imaging compatible components. The drive mechanism, for example, can be configured without an electric motor. The drive mechanism, in some examples, is included in an MRI or MRI head coil. The drive mechanism can be coupled to one or more wires or umbilicals such that a translation of the one or more wires or umbilicals affects one or more of a longitudinal displacement of the holder and a rotation of the holder. A controller, in some implementations, processes position control signals for setting and/or monitoring a position of the holder (e.g., via an input interface to the wires or umbilicals), and issues subsequent position control signals to manipulate positioning of the holder (e.g., via an output interface to the wires or umbilicals).

The system or method, in some implementations, includes a guide mechanism that is attachable to a surface of a patient. The guide mechanism, for example, can include a base structure configured to remain stationary relative to the patient when the guide mechanism is attached to the surface of the patient in a locked state. The guide mechanism can further include a tilt portion that is coupled to the base structure and provides an adjustable tilt between a trajectory of the drive mechanism and the base structure. The guide mechanism can further include a rotation portion that provides an adjustable rotation of the tilt portion relative to the base structure.

The controller, in some implementations, is configured to process a sequence of the position control signals to direct the guide mechanism to move the holder during treatment. For example, the controller can be programmed to move the holder to a first position for effecting the treatment to the tissue at a first portion of the tissue that coincides with the first position and then move the holder to a second position for effecting the treatment to the tissue at a second portion of the tissue that coincides with the second position.

During treatment, in some implementations, a workstation transmits the position control signals to the controller and displays feedback images (e.g., MRI images and/or thermometry images) of the tissue to a user of the workstation. The workstation, for example, can continuously display the thermometry images of the tissue during the treatment to the tissue at the first and second portions of the tissue, and while the holder moves between the first and second positions.

In some implementations, an imaging system receives images of the tissue and the treatment device and analyzes the images to monitor control of positioning and/or therapeutic energy delivery within the tissue. For example, the imaging system may process, in real time, the images of the tissue and the treatment device, as well as the thermometry images of the tissue to forecast errors or interruptions in the treatment to the tissue. Responsive to the analysis, the imaging system may display, via the workstation, an appropriate warning. Position control signals may be updated and transmitted by the workstation to the controller based on one or more of the images, as the images are received by the workstation in real time.

In some implementations, treatment is delivered via an energy emission probe, such as an ultrasonic applicator or laser probe. The energy emission probe, in some examples, may include one or more emitters, such as a radiofrequency emitter, HIFU emitter, a microwave emitter, a cryogenic cooling device, and a photodynamic therapy light emitter. The energy emission probe may include multiple emitters, where the emitters are longitudinally spaced with respect to a longitudinal axis of the energy emission probe.

In some implementations, the energy emission of the probe can be controlled to generate a number of different energy output patterns. The different patterns, for example, can include energy delivered via two or more ultrasonic transducers and/or two or more laser fibers. For example, a laser probe may include a first laser fiber for outputting a symmetrical output pattern with respect to a longitudinal axis of the first laser fiber and a second laser fiber for outputting an asymmetrical output pattern with respect to a longitudinal axis of the second laser fiber. In another example, an ultrasonic applicator may include a first ultrasonic transducer for outputting a first ultrasonic frequency and a second ultrasonic transducer for outputting a second ultrasonic frequency.

The energy output pattern, in some implementations, includes a pulsed output pattern. For example, a higher power density may be achieved without causing tissue scorching or carbonization by pulsing a high power laser treatment for x seconds with y seconds break between so that tissue in the immediate vicinity of the treatment area has an opportunity to dissipate. In a particular example, the laser pattern may be active for two seconds and inactive for one second.

In some implementations, the treatment pattern includes effecting treatment while simultaneously moving the probe (e.g., linearly and/or rotationally). For example, an ultrasonic probe may be rotated while an emission pattern is simultaneously adjusted to effect treatment at a desired depth based upon a particular geometry of a region of interest (ROI) including a targeted tissue area. In one embodiment, the ROI includes multiple targeted tissue areas, which are treated either concurrently, consecutively, or in succession. In this manner, for example, while the ultrasonic treatment beam is focused upon a radial portion of the tumor having a depth of 1.5 centimeters, the power density of the HIFU probe may be tuned for this first treatment depth. Upon rotation to a second radial portion of the tumor may have a depth of 2 centimeters, the power density of the HIFU probe may be increased accordingly to tune for this second treatment depth of 2 centimeters.

An energy source generates energy for the probe. In some implementations, the workstation transmits energy control signals to the energy source. The workstation, for example, may be configured to process a sequence of the energy control signals to first effect a symmetrical treatment area with respect to the tissue, via the probe, and subsequently effect an asymmetrical treatment area with respect to the tissue, via the probe, after the symmetrical treatment. In a particular example, the workstation may be configured to process a sequence of position and laser control signals to move the holder to a first position for effecting the treatment to the tissue at a first portion of the tissue that coincides with the first position, effect a symmetrical treatment to the first portion of the tissue with the first laser fiber, move the holder to a second position for effecting the treatment to the tissue at a second portion of the tissue that coincides with the second position, and effect an asymmetrical treatment to the second portion of the tissue with the second laser fiber. During treatment, the workstation may be configured to display thermometry images of the tissue continuously and concurrently with processing control signals specifying the position and energy associated with the symmetrical and asymmetrical treatments.

In some implementations, the system or method includes a guide sheath configured to accept two or more probes associated with different energy modalities as the treatment device. The modalities may include, for example, laser, radiofrequency, HIFU, microwave, cryogenic, photodynamic therapy, chemical release and drug release. The guide sheath may include one or more off-axis lumens for positioning an emitting point of one or more of the number of probes at an off-axis angle.

A system in accordance with this disclosure incorporates, in an embodiment, MRI-compatible energy emission probes and/or other treatment devices and accessories for controlled delivery of thermal therapy to a number of locations and tumor sizes within a brain. The system, however, is not limited to MRI-guided thermal therapy, as other therapies such as computer tomography (CT) are utilized in other embodiments. Further, this disclosure refers to an MRI scanner as an exemplary medical imaging machine, which may be referred to herein as an MRI.

I. Overview

Turning to FIG. 1, in certain embodiments, an environment 100 for intracranial therapy includes an interface platform 102 (herein an interface platform or interface console), a system electronics rack 104 and components (herein rack), and a control workstation 106 (herein workstation). The interface platform 102 may be used to manipulate and monitor therapy equipment related to one or more energy sources, such as probe introduction equipment including, in an embodiment, a probe driver, a probe, and/or a probe holding and alignment device. The probe introduction equipment, in some examples, can include the low profile anchoring system described in FIGS. 5A-5G below or the stereotactic miniframe described in U.S. patent application Ser. No. 13/838,310 to Tyc, filed Mar. 14, 2013 and titled "Image-Guided Therapy of a Tissue," incorporated herein by reference in its entirety. In certain embodiments, the workstation 106 is configured to control the interface platform 102 for control of the energy emission therapy equipment.

The interface platform 102 is secured to a patient table 108 of an MRI system 110. The MRI system 110 may include a head coil and stabilization system (herein stabilization system), an instrument adaptor, and an MRI trajectory wand. Exemplary MRI systems that can be utilized together with the features discussed herein include those manufactured by Siemens AG, Munich, Germany (including the MAGNETOM AVANTO, TRIO, ESPREE, VERIO MRI Systems, which are trademarks and/or trade names of Siemens AG). Further, example MRI systems include those manufactured by General Electric Company, Fairfield, Conn. (including the SIGNA, OPTIMA and DISCOVERY MRI systems, which are trademarks and/or trade names of General Electric Company).

In certain embodiments, all of the above components of the interface platform 102 and the energy emission therapy equipment are MRI compatible, which refers to a capability or limited capability of a component to be used in an MRI environment. For example, an MRI compatible component operates and does not significantly interfere with the accuracy of temperature feedback provided by the MRI system operating with exemplary flux densities including: magnetic flux densities of 1.5 T or 3.0 T, where no hazards are known for a specified environment (e.g., 1.5 T or 3.0 T). Compatibility can also be defined with respect to one or more other magnetic flux densities, including at least 0.5 T, 0.75 T, 1.0 T, 2 T, and 5 T.

In certain embodiments, the system electronics rack 104 includes cables, penetration panels and hardware that effectuate mechanical, electrical, and electronic operation of the energy emission therapy equipment and the MRI system 110. The system electronics rack 104 may further be used to power and route control signals and/or communications for the control workstation 106.

The workstation 106 includes a display that displays a user interface, e.g., a graphical user interface (GUI) and/or a command line interface that enables a user to plan a treatment procedure and interactively monitor the procedure, the interface platform 102, and the entire MRI system 110. In certain embodiments, the user interface also provides the user, e.g., a medical professional, the ability to directly control the energy emission therapy equipment including an energy source associated therewith, and therefore, enables directly control of the application of the therapy to the patient.

Figure 2:
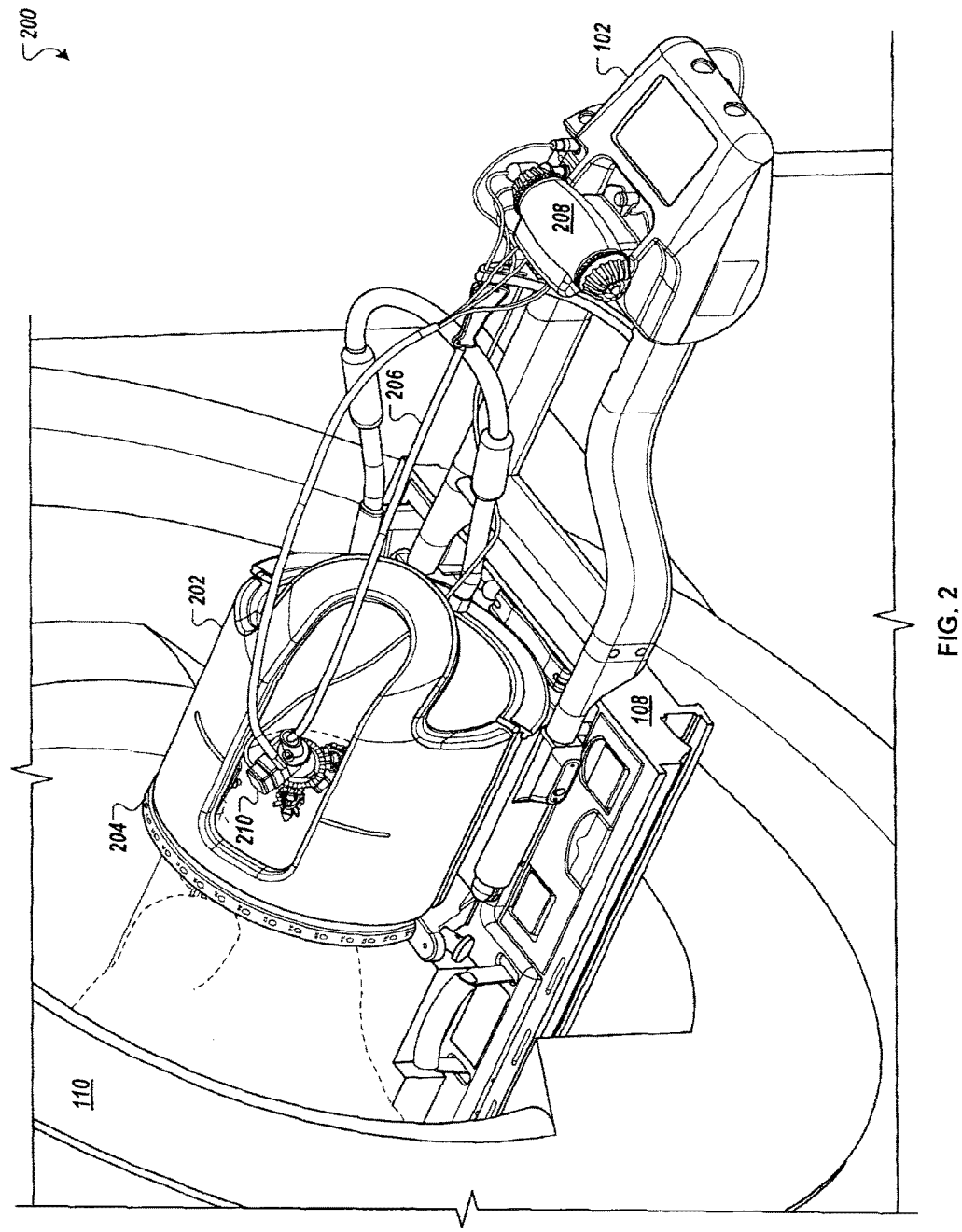
FIG. 2 is an illustration of a perspective view of a patient inserted into an MRI, with a head fixation and stabilization system installed.

Turning to FIG. 2, an exemplary position of a patient on the patient table 108 of the MRI system 110 is illustrated. The interface platform 102 is secured to the patient table 108 together with a head coil 202 and stabilization system, which is a head fixation device that immobilizes a patient's head. The stabilization system includes a head fixation ring 204. A probe 206 and probe driver 208 are coupled to probe introduction equipment 210, and to the interface platform 102 via umbilicals. A cable, for example, can be used to provide data, laser, fluid, etc. connections between the probe 206, probe driver 208, and interface platform 102 and the electronics rack 104 in the MRI equipment room (as illustrated in FIG. 1).

The probe introduction equipment 210, in certain embodiments, includes at least a portion that is detectable by the MRI system (e.g., included in temperature data that is displayed by an imaging portion of the MRI system) and is used for trajectory determination, alignment, and guidance of the probe 206. An MRI trajectory wand (e.g., an MRI detectable, fluid-filled tube) may be placed into the probe introduction equipment 210, for example, to confirm a trajectory, associated with an intended alignment, to a targeted tissue region, via MRI. After confirmation, the probe 206 may be introduced into the probe introduction equipment 210 to effect surgery or therapy.

The probe 206 may be composed of MRI compatible materials that permit concurrent energy emission and thermal imaging, and can be provided in multiple lengths, cross-sectional areas, and dimensions. Types of probes that can be utilized with the components and procedures discussed herein include RF, HIFU, microwave, cryogenic, and chemical release probes; the chemical release probes may include photodynamic therapy (PDT), and drug releasing probes. Treatments in accordance with the descriptions provided in this disclosure include treatments that ablate (i.e., "treat") a tissue to destroy, inhibit, and/or stop one or more or all biological functions of the tissue, or otherwise cause cell damage or cell death that is indicated by a structural change in cells of the targeted tissue area. Ablation can be effected by laser, RF, HIFU, microwave, cryogenic, PDT and drug or chemical release. A corresponding probe and/or other instrument, such as a needle, fiber or intravenous line can be utilized to deliver one or more of these ablation agents intracorporeally or percutaneously and proximate to, in the vicinity of, abutting, or adjacent to a targeted tissue area so as to effect treatment. The probe 206 can be a gas-cooled probe so as to control delivery of the energy to the targeted tissue area. The length and diameter of the probe 206 is preselectable based on the targeted tissue area and/or the ROI. The probe 206, in some particular examples, can be a laser delivery probe that is used to deliver laser interstitial thermal therapy or a HIFU applicator that is used to deliver HIFU interstitial thermal therapy.

Figure 3:
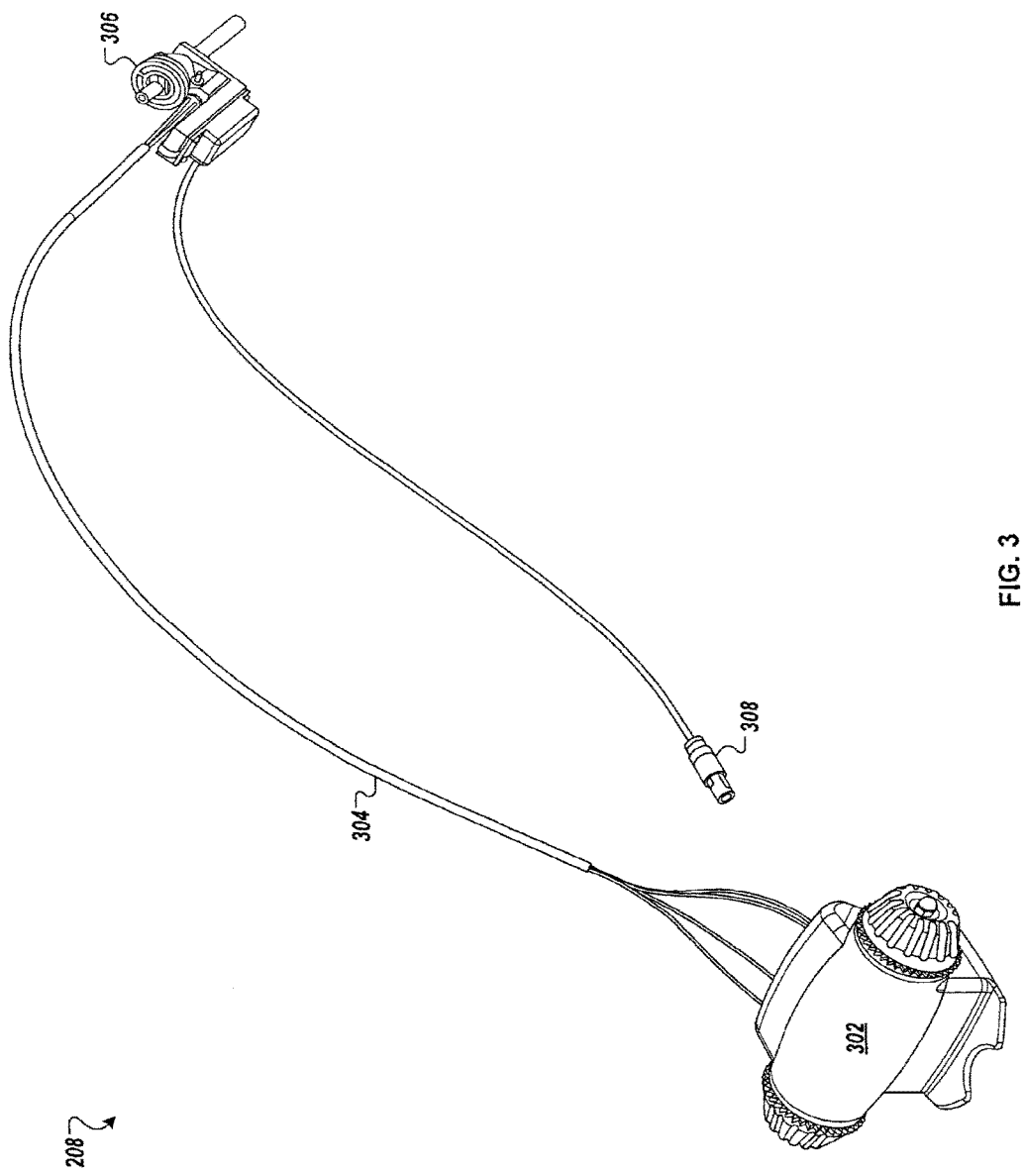
FIG. 3 illustrates a probe driver.

The probe driver 208 controls positioning, stabilization and manipulation of the probe 206 within a specified degree of precision or granularity. Turning to FIG. 3, the components of the probe driver 208 generally include a commander 302, umbilicals 304, a follower 306, and a position feedback plug 308 that receives position feedback signals from, for example, potentiometers within the follower 306. The probe 206 (illustrated in FIG. 2) can be inserted into the follower 306, and the follower 306 can control a rotational and longitudinal alignment and/or movement of the probe 206. The probe driver 208 can further include a rotary test tool (not illustrated) that can be used during a self-test procedure to simulate attaching a probe to the follower 306. An exemplary probe driver that can be utilized in accordance with the various aspects presented in this disclosure is described in U.S. Pat. No. 8,728,092 to Qureshi, entitled "Stereotactic Drive System" and filed Aug. 13, 2009, the entirety of which is incorporated herein by reference.

The probe driver 208 (illustrated in FIG. 2) is mounted to the interface platform 102. The position feedback plug 308 (illustrated in FIG. 3) connects to the interface platform 102 in order to communicate the position of the probe 206 to the user and/or the workstation 106 (illustrated in FIG. 1). The probe driver 208 is used to rotate or translate, e.g., by extending or retracting the probe 206. The probe driver 208, in a particular example, can provide, at a minimum, a translation of 20-80 mm, 30-70 mm, 40-60 mm or 40 mm, with a maximum translation of 60 mm, 80 mm, 100 mm, 120 mm or 60-150 mm. The probe driver 208, further to the example, can also provide, at a minimum, a rotation of 300°-340°, with a maximum rotation of 350°, 359°, 360°, 540°, 720° or angles therebetween.

Returning to FIG. 1, in certain embodiments, the workstation 106 outputs signals to the MRI system 110 to initiate certain imaging tasks. In other implementations, the workstation 106 outputs signals to an intermediary system or device that causes the MRI system 110 to initiate the imaging tasks. In certain embodiments, the workstation 106 additionally outputs signals to the electronics rack 104. The electronics rack 104 includes various actuators and controllers that control the thermal therapy devices, such as, in some examples, a cooling fluid pressure and/or a flow rate of the cooling fluid, and a power source that powers a thermal therapy device. In one example of a thermal therapy device, the power source is a laser source that outputs laser light via an optical fiber. As illustrated in FIG. 1, the electronics rack 104 is located in an MRI Equipment Room and includes storage tanks to hold the cooling fluid, one or more interfaces that receive the signals from the control workstation 106 and/or a separate MRI workstation, an energy emission source (e.g. laser), and an output interface. One or more of the interfaces are connected with or include physical wiring or cabling that receives the signals and transmits other signals, as well as physical wiring or cabling that transmit energy to corresponding components in the MRI Scan Room through a portal that routes the signals and/or energy in a manner that minimizes any interface with or by the MRI system 110. The wiring or cabling are connected at or by the interface platform 102 to corresponding components to effect and actuate control of a thermal therapy device and/or an associated thermal therapy session. Controlling the thermal therapy device, for example, by a user in the MRI control room prevents the introduction of noise to the MRI system, which includes the MRI cabin. The remotely controlled procedure enhances thermal therapy efficiency and accuracy by preventing heating loss due to stopping and restarting energy application.

In certain embodiments, the system is indicated for use to ablate, necrotize, carbonize, and/or coagulate the targeted tissue area (e.g., an area of soft tissue) through interstitial irradiation or thermal therapy, in accordance with neurosurgical principles, with a HIFU thermal therapy device. The HIFU thermal therapy device or probe includes ultrasonic transducers for directing ultrasonic energy at the targeted tissue area, causing the tissue to heat. The ultrasonic beam of the HIFU probe can be geometrically focused (e.g., using a curved ultrasonic transducer or lens) or electronically focused (e.g., through adjustment of relative phases of the individual elements within an array of ultrasonic transducers). In an ultrasonic transducer array, the focused beam can be directed at particular locations, allowing treatment of multiple locations of an ROI without mechanical manipulation of the probe. The depth of treatment can be controlled by adjusting the power and/or frequency of the one or more transducers of the HIFU probe.

In certain embodiments, either additionally or alternatively to HIFU thermal therapy, a laser-based thermal therapy is utilized in the MRI system. Laser probes of a variety of outputs can be utilized, including, in some examples, laser probes emitting laser light having wavelengths of 0.1 nm to 1 mm, and laser probes emitting laser light in one or more of the ultraviolet, visible, near-infrared, mid-infrared, and far-infrared spectrums. Types of lasers used with respect the laser probe include, for example, gas lasers, chemical lasers, dye lasers, metal-vapor lasers, solid-state lasers, semiconductor lasers, and free electron lasers. In a particular example, one or more wavelengths of the laser light emitted by the laser probe are within the visible spectrum, and one or more wavelengths of the laser probe are within the near-infrared spectrum.

In certain embodiments, the environment 100 can be utilized for planning and monitoring thermal therapies effected via MRI-imaging, and can provide MRI-based trajectory planning for the stereotactic placement of an MRI compatible (conditional) probe. The environment 100, in certain embodiments provides real-time thermographic analysis of selected MRI images and thus, temperature feedback information and/or thermal dose profiles for the targeted tissue area. For example, thermographic analysis of the MRI images can provide real-time verification of cellular damage in a targeted tissue area that corresponds to necrosis, carbonization, ablation, and/or coagulation. In another example, thermographic analysis can be used to monitor tissue surrounding a periphery of an ROI to ensure minimal if any damage to healthy tissues. Components of the environment 100 may assist in guiding, planning, adjusting, performing and confirming a thermal therapy session and trajectories associated therewith.

A procedure includes, generally, identifying an ROI and/or associated targeted tissue areas in a patient that should be treated, planning one or more trajectories for treating the tissue, preparing the patient and components for the treatment, and performing the treatment. Aspects of the various parts of the treatment are described throughout this disclosure, and an exemplary sequence of treatment steps is illustrated in FIGS. 4A and 4B.

Figure 4A:
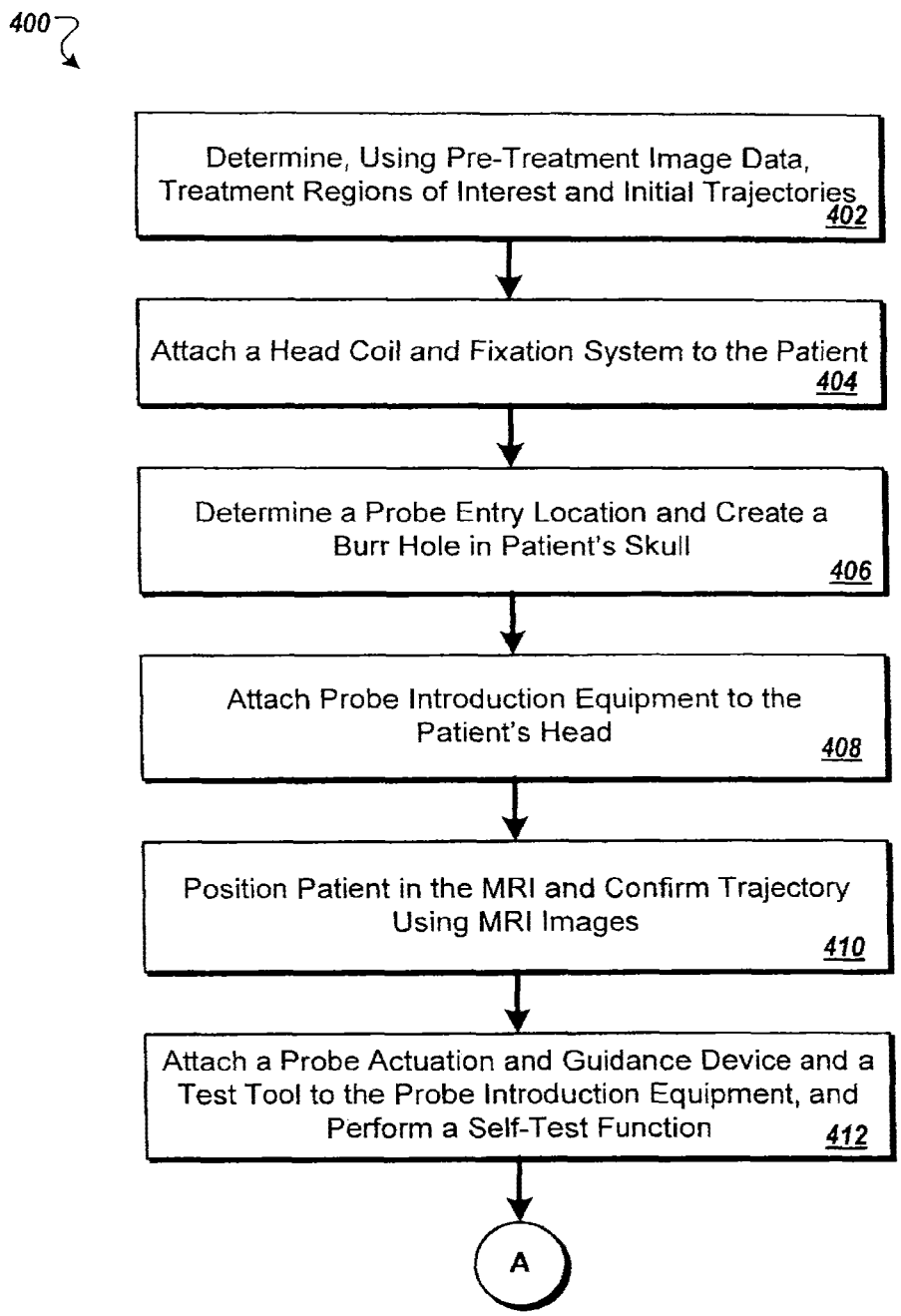
FIGS. 4A and 4B are flow charts illustrating an exemplary procedure for treating a patient.
Figure 4B:
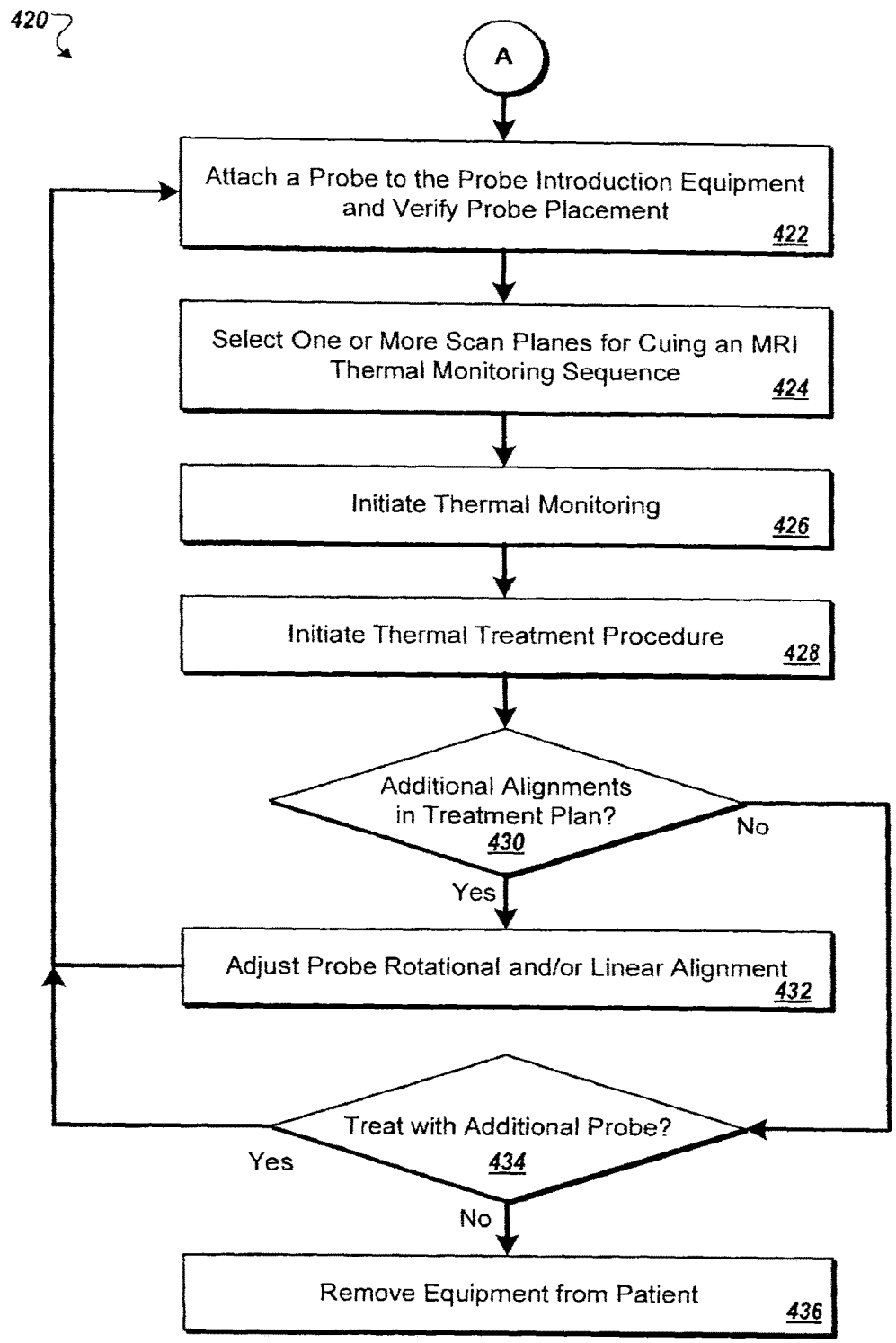

Turning to FIG. 4A, a process flow diagram illustrates an exemplary method 400 for pre-planning a treatment of a patient. In pre-planning the thermal therapy session, in certain embodiments, pre-treatment Digital Imaging and Communications in Medicine (DICOM) image data is loaded and co-registered, for example, via the workstation 106 (illustrated in FIG. 1). Using the DICOM image data, one or more ROIs and/or targeted tissue areas and one or more initial trajectories can be determined and set (402).

In preparation for treatment, in certain embodiments, a head coil and fixation system is attached to the patient (404), for example by positioning the head coil and stabilization system on the surgical table. The patient can be immobilized using a head fixation ring. To ensure stable imaging, for example, the patient's head can be secured with the head fixation ring and remain fixed for the entire imaging portion of the flow chart in FIG. 4A. An example head fixation system is described below in relation to FIGS. 6A through 6E.

Prior to applying thermal energy to an ROI, a probe entry location into the skull is identified. In certain embodiments, a burr hole is drilled in the skull (406). The burr hole may be drilled prior to attachment of probe introduction equipment (e.g., a miniframe, anchoring device, guide stem, instrument sheath, etc.). A twist-drill hole, in certain embodiments, can be created following a trajectory alignment of the probe introduction equipment. The twist-drill hole can have a size of 1-5 mm, 2 mm, 3 mm, 4 mm or 4.5 mm.

The probe introduction equipment, such as a stereotactic miniframe or low profile anchoring device, in certain embodiments, is attached to the patient's head (408). Probe aligning equipment, such as the miniframe or guide stem, can then be aligned along the intended trajectory, for example using image-guided navigation. After attaching the probe introduction equipment, the head coil can be attached. An exemplary head coil system is described below in relation to FIG. 7. Depending on a process flow that is specific to a surgical center, the interface platform may be attached prior to or after MRI trajectory confirmation. The order of steps in a site-specific process may be determined based on members of MRI or surgical support team and may be determined during on-site training with respect to the MRI system. The interface platform (IP) is attached to the head end of the head coil and stabilization system. Then, the IP power and motor plugs are connected.

In certain embodiments, the patient is positioned in the MRI cabin, and MRI imaging is performed to confirm a trajectory (410) associated with a thermal therapy device and/or probe introduction equipment. For example, an MRI trajectory wand may be inserted into the probe introduction equipment for use in confirming its trajectory. The trajectory of the probe introduction equipment, for example, can be evaluated using MRI imaging prior to inserting a probe into the brain. Volumetric imaging or volumetric visualization may be captured to include the entire head and full extent of the probe introduction equipment. Along with trajectory confirmation, in some examples, beam fiducial marker detection may also be performed. For example, the captured images may also display a position of a beam fiducial marker located in a portion of the probe introduction equipment. This marker can be detected and identified by the MRI imaging system and method to store an orientation of the physical direction of the probe. The captured images, in implementations where pre-treatment image data is not available, can be used for planning a thermal therapy session.

In certain embodiments, a probe actuation and guidance device (e.g., a follower) and a test tool are attached to the probe introduction equipment, to provide positional feedback for a self-test function (412). The self-test function, for example, may be used to confirm that inputs to the probe actuation and guidance device, (e.g., from the workstation), accurately and/or precisely drive the probe. Upon completing the self-test function, the rotary test tool may be removed. Upon completing the procedure described in relation to FIG. 4A, the procedure equipment may be introduced and the procedure initiated.

Turning to FIG. 4B, a process flow diagram illustrates an exemplary method 420 for a treatment procedure. In certain embodiments, a probe is attached and inserted into the probe introduction equipment and/or the patient's skull (e.g., secured for manipulation via the probe actuation and guidance device) (422). Exemplary implementations of neurosurgical probes are discussed in below under the section entitled "Probes." It is noted that different types of probes can be used in conjunction different types of thermal therapy, for example, when an ROI is not in the brain. An MRI scan can then be conducted to ensure probe alignment is correct and confirm movement and delivery of the probe along the intended trajectory. In one example, the acquired image data can be displayed, along with pre-planning image data by the workstation 106. Using a graphical user interface (GUI), a user can adjust the probe displayed by the GUI by interacting with, for example, the GUI to match the probe artifact on the acquired image to ensure that the alignment and arrangement of the probe as physically placed in the probe introduction equipment and inserted into the patient coincides with the rendered probe at the workstation. The probe's trajectory, for example, can be adjusted to a desired position for delivering thermal energy, via interaction with the GUI. Further, the probe's rotational position can also be adjusted to a desired direction or angle for thermal delivery, via interaction with the GUI. Once the probe rendering presented by the GUI matches the probe artifact on the display, the user may confirm the trajectory via the GUI. In certain embodiments, one or more scan planes are selected for cuing a thermal monitoring sequence via the MRI system's sequence protocol list (424). In another embodiment, a 3D volume is selected and in yet another embodiment, a linear contour is selected. Parameters associated with scan plane, in some examples, can be entered by a user via a workstation connected with the MRI system or directly into the thermal monitoring sequences protocol's geometry parameters of the MRI.

In certain embodiments, temperature feedback information and/or thermal dose profiles are initialized and monitored (426). For example, under a noise masking heading of the workstation interface, at least three reference points (e.g., six, twelve, twenty, etc.) can be selected by the user at the periphery of the ROI. The ROI, for example, may include an overlaid, orange noise mask in one or more image monitoring view panes to illustrate the intended thermal delivery area. The noise masking may be used to improve accuracy of temperature monitoring during tissue treatment.

In certain embodiments, energy delivery via the probe is actuated to begin the thermal therapy session (428). For example, once "Ready" indicator or the like is displayed under a laser status heading of the GUI at the workstation, the user may depress a foot pedal operatively connected to the workstation to deliver thermal energy to the ROI or a targeted tissue area within the ROI. Thermal energy can then be either continuously or intermittently delivered while monitoring thermal dose profiles, which can be presented as contours that are overlaid onto one or more (e.g., three) thermal monitoring view panes rendered by the GUI of the work station. Thermal delivery may be halted as desired or as necessary by releasing the foot pedal. The view panes, for example, may display an energy dose profile or thermal dose profile supplied by the probe, with respect to a specified time period and/or a specified targeted tissue area or ROI; the thermal dose or energy dose profile can be displayed as a succession of temperature gradients. The thermal dose profiles and/or the temperature gradients permit the determination of an extent of cellular damage in the targeted tissue area and/or other effects upon the targeted tissue area occurring as a result of the thermal therapy.

Once a thermal dose for a particular alignment and positioning of the probe is completed, if further probe alignments are desired within the treatment plan (430), a rotational and/or linear alignment of the probe may be adjusted (432) by translating or rotating the probe. For example, an energy output of the probe may be terminated and then the probe may be subjected to linear translation and/or rotational movement, which can be controlled, for example, by a probe driver (a particular implementation of which is illustrated in FIG. 3). After adjusting the probe alignment, in certain embodiments, the process returns to step 422 to verify a current placement of the probe. In certain embodiments, a second thermal treatment procedure is not initiated (e.g., when repeating step 428) until one or more targeted tissue areas within the ROI returns to a baseline body temperature. The thermal dose associated with the one or more targeted tissue areas in the ROI, as described in relation to steps 422 through 432, may continue at various probe rotational and/or linear alignments until the entire ROT has been treated.

Upon determining that the thermal therapy is complete (430), should treatment with an additional probe be needed or desired (434), the procedure can be repeated by attaching the new probe to the probe introduction equipment and verifying probe placement (422). If, instead, the second probe was initially included within the probe introduction equipment (e.g., via a separate lumen in a guide sheath in relation to the first probe), the user may initiate positioning of the second probe, for example, via the GUI, and verify placement of the second probe (422). A multi-probe configuration is described in greater detail in relation to FIG. 5I.

If the second probe is being deployed to treat the same ROI or the same targeted tissue area at the same linear and rotational alignment(s) associated with the first probe, in certain embodiments, step 424 involving selection of scan planes for the cuing the thermal monitoring sequence may be skipped. If, instead, a second probe is deployed at a different linear position or a different trajectory, step 422 may be performed to confirm the trajectory and alignment of the second probe.

When the thermal therapy is complete (434), in certain embodiments, the patient is removed from the MRI bore and the probe, probe actuation and guidance device, and probe introduction equipment are detached from the patient. The bore hole may be closed, for example, at this time.

II. Low Profile Probe Introduction Equipment

A. Low Profile Skull Anchoring Device

Figure 5A:
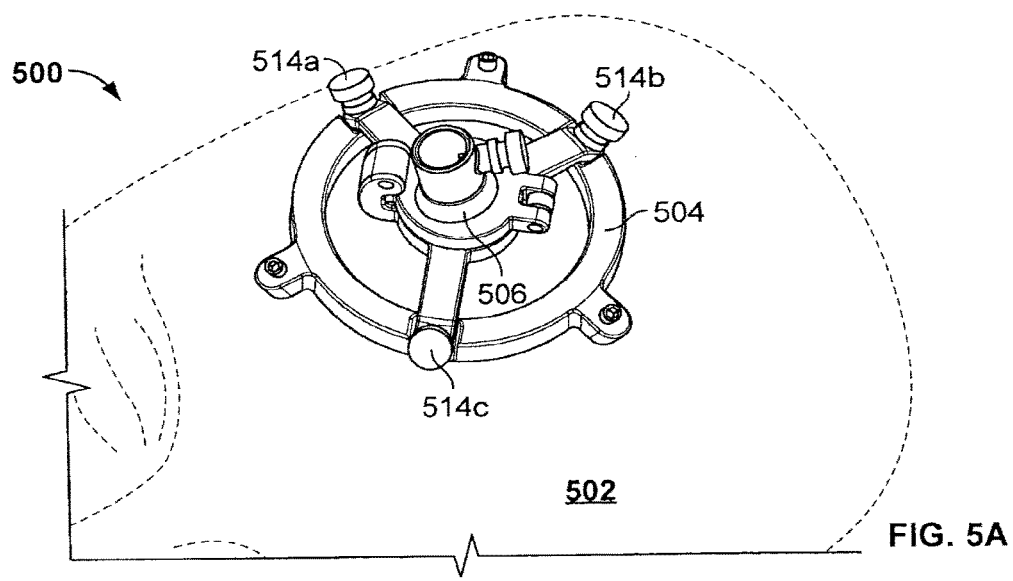
FIGS. 5A through 5E illustrate a low profile skull anchoring device and example guide stems.
Figure 5B:
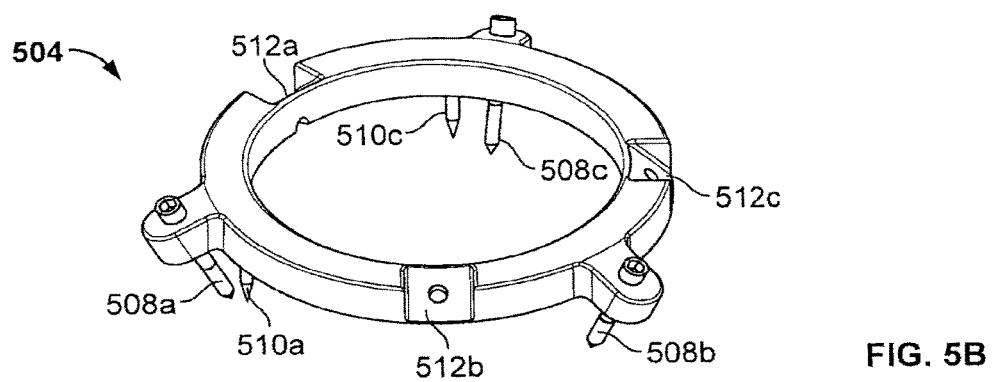

In certain embodiments, when preparing for an intracranial neurosurgical procedure, a patient 502 is fitted with a low profile skull anchoring device 504, as illustrated in an exemplary mounting illustration 500 of FIG. 5A. The low profile skull anchoring device 504 may be releasably attached to the head of the patient 502, for example, using three or more bone anchors mounted to the skull of the patient 502. Turning to FIG. 5B, the low profile skull anchoring device 504 includes three bone screws 508 for connecting to bone anchors within the skull of the patient 502, as well as pins 510 for further securing the low profile skull anchoring device 504 to the head of the patient 502 and for ensuring that the low profile skull anchoring device 504 mounts above the surface of the head of the patient 502. In this way, there will be minimal or no compression of the patient's scalp, and frameless, on-trajectory access is provide, as discussed in further detail below. In one embodiment, the low profile skull anchoring device 504 has an oval or an oblong shape.

In one embodiment, the screws 508 and pins 510 are composed of, for example, titanium. It should be noted that the screws 508 and the pins 510 are not necessarily limited to three pins; the number of screws 508 and pins 510 is the number which is necessary to provide sufficient rigidity. The screws 508 and pins 510 may be evenly spaced around the circumference of the low profile skull anchoring device 504 (e.g., positioned approximately every 120 degrees). In another embodiment, the screws 508 and pins 510 are positioned at unequal distances apart, for example, based on an irregular skull curvature. In yet another embodiment, the screws 508 and the pins 510 are movable with respect to the low profile skull anchoring device 504. In still another embodiment, the screws 508 are replaced with a sufficiently rigid adhesive or a staple, each of which provide sufficient rigidity to allow for the drilling of a burr hole in the skull.

Due to the low height of the low profile skull anchoring device 504, the medical team is provided with greater access for lateral trajectories of biopsy, probes, and other apparatus to be inserted intracranially into the patient 502 via the low profile skull anchoring device 504. This may be especially useful when working within the confines of an MRI bore, for example during MRI-guided thermal therapy treatments. As such, the low profile skull anchoring device 504 may be composed of MRI compatible materials and, optionally, include MRI visible markers for aligning a desired trajectory or defining a particular direction relative to the low profile skull anchoring device 504. In another example, the low profile skull anchoring device 504 may allow easier access to back-of-the-head entry trajectories, such as trajectories used in performing epilepsy treatments. A mounting height of the low profile skull anchoring device 504, for example, may be thirty millimeters or less from the surface of the skull of the patient 502.

In some implementations, the low profile skull anchoring device 504 includes one or more fiducial markers for reference within an MRI scan. For example, the low profile skull anchoring device 504 may include at least three fiducial markers used, in an MRI scan, to identify a position and orientation of the low profile skull anchoring device 504 as attached to the surface of the skull of the patient 502. In a particular example, three fiducial markers, at least one of which having a unique length, width, and/or shape in comparison to the others, may be positioned upon the low profile skull anchoring device 504 to allow for visual display and confirmation of a position and orientation of the low profile skull anchoring device 504 as attached to the skull of the patient 502. The fiducial marker(s) may be held in place via any suitable connector including, but not limited to, an adhesive or the like.

B. Removable Guide Stem

Turning to FIG. 5A, the low profile skull anchoring device 504 includes a removable guide stem 506. The removable guide stem 506, in some examples, may lock to the low profile skull anchoring device 504 using a screw mechanism, keyed locking mechanism, or other connector configured to firmly connect the removable guide stem 502 to the low profile skull anchoring device 504 with relative ease of removal.

Figure 5C:
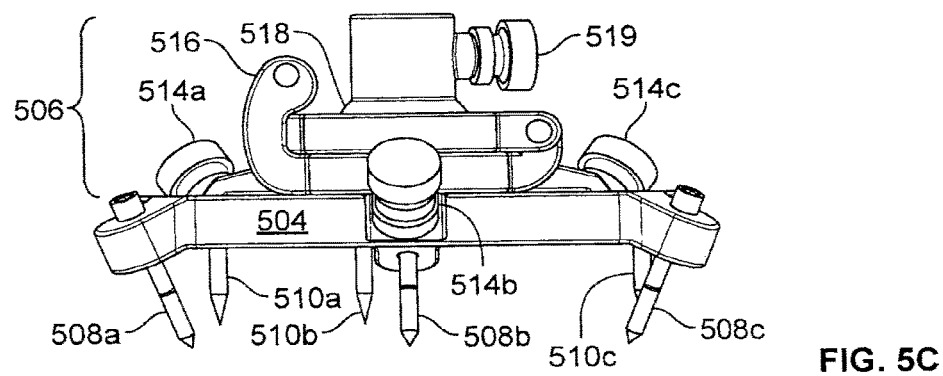

Turning to FIG. 5B, the exemplary the low profile skull anchoring device 504 includes three connection points 512 for securing the removable guide stem 506 to the low profile skull anchoring device 504. The removable guide stem 506, for example, may include a series of guide stem connectors 514 (e.g., screws or locking pins) which mate with the connection points 512 of the low profile skull anchoring device 504, as shown in FIGS. 5A and 5C. In one embodiment, the alignment of the guide stem connectors 514 and the connection points 512 differs based on a skull curvature of the patient.

A central cylindrical portion of the removable guide stem 506 is configured to receive various adapters and/or instruments such as, in some examples, drill bits, biopsy needles, and treatment probes. The central cylindrical portion of the removable guide stem 506, in certain embodiments, is rotatably adjustable, allowing an orientation of central cylindrical portion of the removable guide stem 506 to be manipulated to align the probe in accordance with a desired trajectory. Upon alignment, in certain embodiments, a locking mechanism 516 may be actuated to lock the central cylindrical portion of removable guide stem 506 into place at the set alignment.

Turning to FIG. 5C, the removable guide stem 506 may include, for example, a ball joint 518 for establishing an adjustable trajectory for passing instruments to the skull of the patient 502 via the central cylindrical portion of removable guide stem 506. In certain embodiments, the central portion has another geometric or polygonal shape that corresponds to a cross-section of the probe. In certain embodiments, interior portions of the central cylindrical portion of the removable guide stem 506 are deformable so as to cover an outer surface of the probe. In still other embodiments, the interior portions of the central cylindrical guide stem are comprised of shape memory alloys that have a transition temperature that exceeds a maximum temperature associated with a specified thermal therapy.

The ball joint 518 can achieve a number of trajectories that is based on the granularity with which the ball joint 518 is manipulated. Upon setting the trajectory of the central cylindrical portion of removable guide stem 506, for example, the ball joint 518 may be clamped into position using the locking mechanism 516. In one embodiment, the locking mechanism 516 is a cam lock. In another embodiment, the locking mechanism 516 is a ring clamp. In still another embodiment, the locking mechanism 516 has a screw engagement.

Figure 5D:
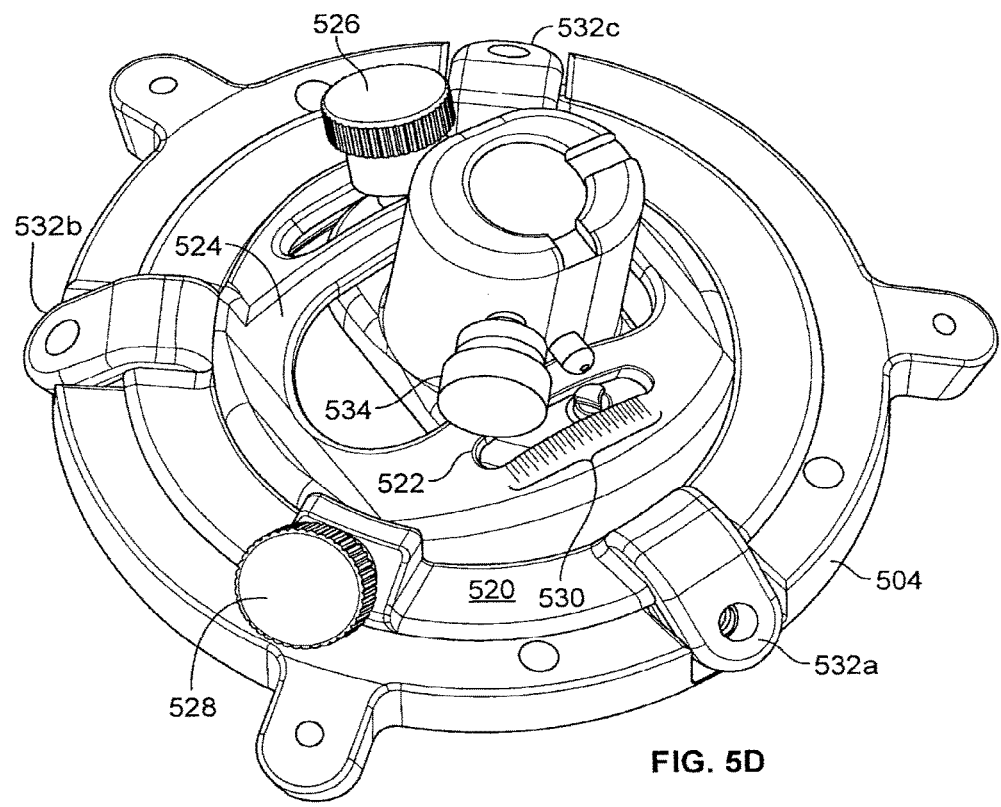
Figure 5E:
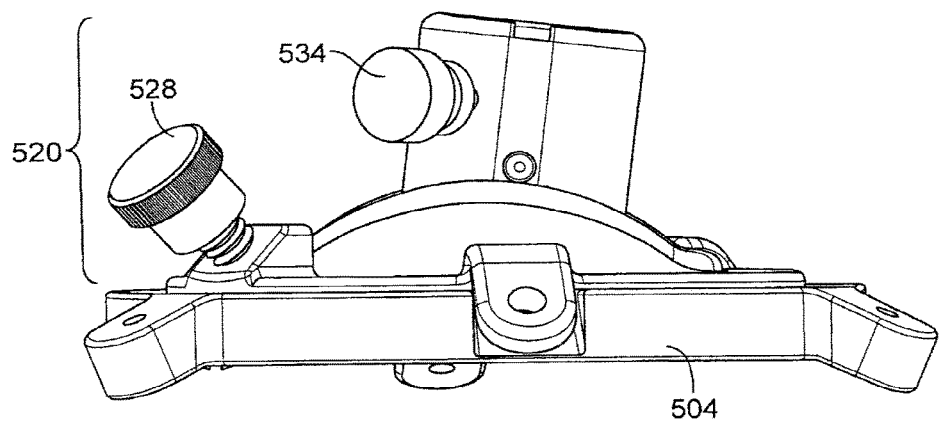

Turning to FIGS. 5D and 5E, illustrative examples of a removable guide stem 520 including both a tilt adjustment 522 and a rotation adjustment 524 are shown. The separate tilt adjustment 522 and rotation adjustment 524, for example, may be used to more precisely adjust a trajectory of the central cylindrical portion of removable guide stem 520. Upon adjusting the tilt adjustment 522, for example, a tilt lock mechanism 526 (e.g., screw, pin and slot, etc.) may be activated to hold the central cylindrical portion of removable guide stem 520 at the tilt position. In another example, upon adjusting the rotation of the central cylindrical portion of removable guide stem 520, for example by turning the rotation adjustment 524, a rotation lock mechanism 528 (e.g., screw, pin and slot, etc.) may be activated to hold the removable guide stem 520 at the selected rotation. In an embodiment, either or both of the tilt lock mechanism 526 and the rotation lock mechanism 528 are actuated by a motor. In another embodiment, the motor is wirelessly controlled via a remotely located controller. The removable guide stem 520 is removable during a thermal therapy session, prior to completion of the treatment, and independent of removing the low profile skull anchoring device 504.

In certain embodiments, guide lines such as a set of guide lines 530 are marked on the removable guide stem 520 (or the removable guide stem 506 illustrated in FIG. 5A) to provide a user with an indication of the selected trajectory. For example, an angle of tilt in relation to the low profile skull anchor 504 may be selected via the guide lines 530 (e.g., within a one, two, or five degree angle of adjustment). The guide lines 530, in certain embodiments, are MR indicators, such that an MR image captured of the removable guide stem 520 will allow a software package to register an initial trajectory in relation to the head of the patient (e.g., patient 502 of FIG. 5A).

In certain embodiments, in addition to a tilt and rotation adjustment, either the first removable guide stem 506 or the second removable guide stem 520 may be modified to include an x,y degree of freedom adjustment mechanism (not illustrated). In this manner, a position of the central cylindrical portion of guide stem 506 in relation to a burr hole opening beneath the low profile skull anchor 504 may be adjusted by the user, thus providing on-trajectory access. Rather than the central cylindrical portion of guide stem 506 or 520 being centered within the low profile skull anchor 504, for example, an x,y adjustment mechanism may allow an offset of the central cylindrical portion of removable guide stem 506 or 520. In a particular example, should the burr hole fail to be centered between bone anchors planted within the skull of the patient 502, the central cylindrical portion of guide stem 506 or 520 may be adjusted by up to at least ten to twenty millimeters to be centered above the burr hole using an x,y adjustment mechanism.

In some implementations, the removable guide stem 506 or 520 includes at least one fiducial marker for identifying, via an MRI scan, at least an angle of trajectory of the removable guide stem 506 or 520. If the removable guide stem 506 or 520 additionally includes an adjustment mechanism, fiducial marker(s) may be used to identify the x,y offset of the removable guide stem 506 or 520 relative to the low profile anchoring device 504.

Turning to FIG. 5B, upon removal of the removable guide stem 506 or 520, the skull entry location becomes accessible, for example to allow for formation of a burr hole or to otherwise prepare the skull entry location. After preparation of the entrance, the removable guide stem 506 or 520 may be locked to the low profile skull anchor 504. For example, as illustrated in FIG. 5D, the removable guide stem 520 may be locked to the low profile skull anchor device 504 by attaching screws at three connection locations 532. At any point in a procedure, should access to the entrance be desired, the guide stem 520 may be removed. Removal of the guide stem 520, for example, allows a medical professional quick access to react to bleeding or to adjust the burr hole opening for trajectory correction.

When performing a medical procedure via the low profile skull anchoring device 504, in certain embodiments, the low profile skull anchoring device 504 may first be aligned with screw anchors mounted upon the patient's skull and then screwed to the head of the patient 502, as illustrated in FIG. 5A. The skull entry location may be prepared for treatment during the thermal therapy while the removable guide stem 506 or 520 has been separated from the low profile skull anchoring device 504. Following preparation of the skull entry location, the removable guide stem 506 or 520 may be replaced and its trajectory aligned.

To align the removable guide stem 506, 520 with a desired treatment trajectory, in certain embodiments, the removable guide stem 506, 520 is manipulated via an image guided system (e.g., MRI-imaging system) or manipulated via a trajectory planning module of an MRI-imaging method. The manipulations of the removable guide stem 506, 520, for example, may be performed by a probe actuation and guidance device. In a particular example, as described in relation to the method 400 of FIG. 4A, a test tool may be inserted into the removable guide stem 506, 520, and the test tool may be aligned with pre-treatment image data to determine an initial trajectory. In other implementations, a user manually adjusts the trajectory of the removable guide stem 506, 520. Alignment of the trajectory of the removable guide stem 506, 520, in certain embodiments, is aided by one or more guide lines or fiducial markers upon the surface of the low profile skull anchoring device 504 and/or upon the surface of the removable guide stem 506, 520, such as the guide lines 530 illustrated in FIG. 5D.

Upon positioning the trajectory of the removable guide stem 506, 520, in certain embodiments, the trajectory is locked via a locking mechanism, such as the locking mechanism 516 of FIG. 5C or the locking mechanisms 526 and 528 of FIG. 5D.

After the removable guide stem 502 has been locked into its initial trajectory, in certain embodiments, instruments may be guided into the skull via the removable guide stem 506 or 520. For example, biopsy tools, a thermal treatment probe, medicament delivery probe, or other neurosurgical device may be delivered to a ROI of the brain of the patient via the removable guide stem 506 or 520.

C. Guide Sheath

Figure 5G:
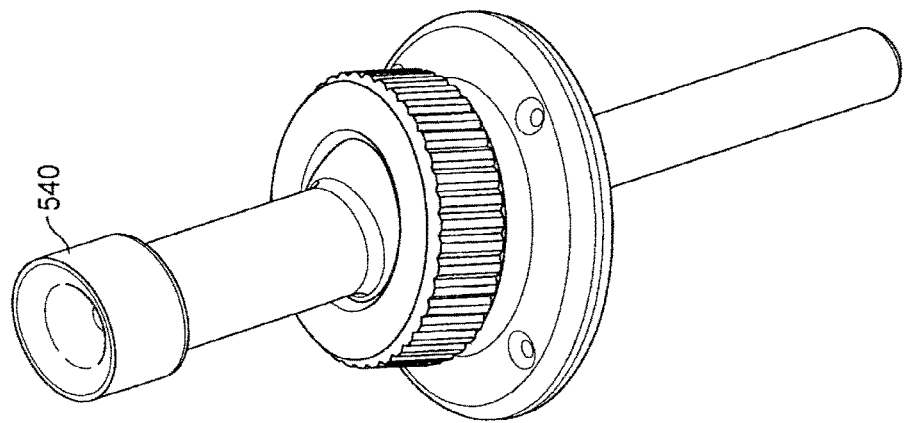
FIGS. 5F and 5G illustrate a guide stem and sheath configured to interconnect with the low profile skull anchoring device.
Figure 5F:
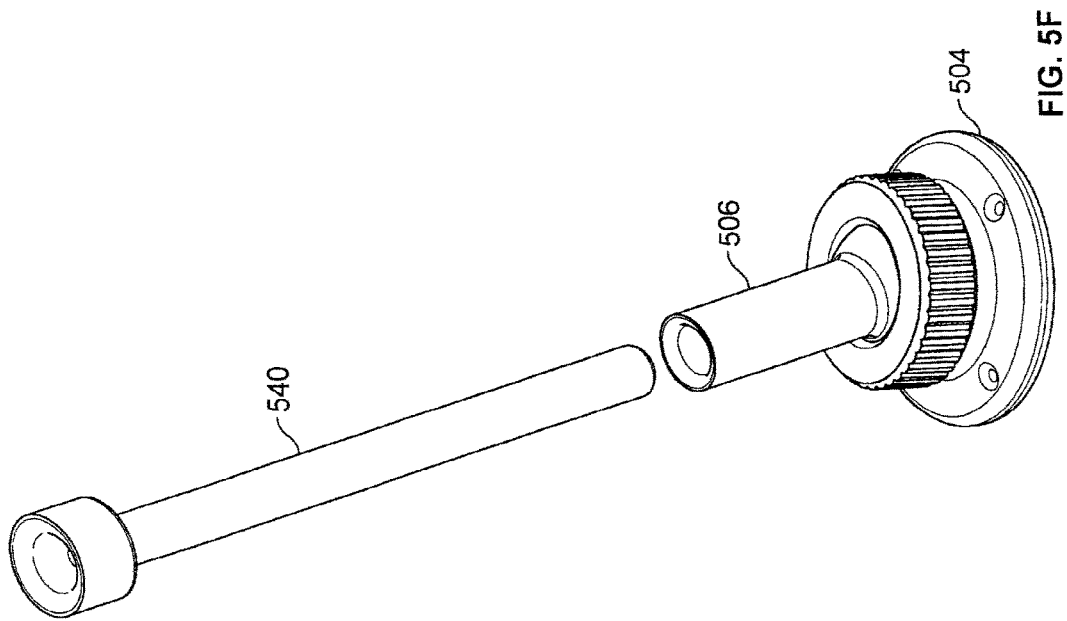

Turning to FIGS. 5F and 5G, in certain embodiments, rather than inserting instruments directly into the removable guide stem 506 or 520, a guide sheath 540 is inserted into the removable guide stem (e.g., removable guide stem 506). The guide sheath 540 may include, for example, one or more distal openings and one or more proximal openings to introduce at least one neurosurgical instrument to the ROI in the patient's brain.

In certain embodiments, instead of using the guide sheath 540 configured for receipt of neurosurgical devices, a hollow trocar may be introduced via the removable guide stem 506 or 520 to prepare an initial entry into a region of the brain. For example, when entering a particularly fibrous area, rather than pushing in directly with a neurosurgical instrument and risking damage to the neurosurgical instrument, a trocar or stylette, for example with a bullet shaped nose and sharp distal opening, may be used to cut a path for the neurosurgical instrument. In other implementations, a stylette or trocar may be introduced to the ROI via the guide sheath 540. In one embodiment, the guide sheath 540 has a shape of a 3D almond. In another embodiment, a ball joint portion of the guide sheath 540 rotates around a track. In yet another embodiment, the probe holder is attached at a non-zero angle to the longitudinal access of at least a portion of the probe.

In certain embodiments, the guide sheath 540 locks to the removable guide stem 506. The guide sheath 540, for example, may be configured to lock to the removable guide stem 506 at a variable linear height depending upon a distance between the skull opening and a ROI. In this manner, the guide sheath 540 may be deployed in proximity to, in the vicinity of, or adjacent to an ROI without abutting or entering the ROI. As such, upon removal of one or more neurosurgical instruments via the guide sheath 540, cells from the ROI will not be able to contaminate other regions of the patient's brain.

Turning back to FIG. 5C, in certain embodiments, a guide stem locking mechanism 519 may be used to clamp the guide sheath 540 at a particular linear depth. The guide sheath 540, in a particular example, may have spaced indentations or other connection points for interfacing with the guide stem locking mechanism 519 (e.g., set screw or spring-loaded plunger). The indentations (or, alternatively, ratcheting teeth) may be positioned at precise measurements (e.g., 1 mm apart) to aid in linear position adjustment. In other examples, the guide sheath 540 and guide stem locking mechanism 519 may be configured to provide positive feedback to a medical professional during adjustment. For example, a linear actuator system such as a rack and pinion may be used to provide precise linear position adjustment (e.g., one "click" per millimeter). Upon adjustment, to lock the guide sheath 540 at the selected linear position, in certain embodiments a cam lock mechanism may be used to engage teeth or depressions within the guide sheath 540. For example, a cam lock mechanism such as the locking mechanism 516 illustrated in FIG. 5C may be used to lock the guide sheath 540 at a selected linear depth.

Turning back to FIG. 5D, the removable guide stem 520 similarly includes a guide stem locking mechanism 534. In other implementations, the guide sheath 540 may directly connect to the low profile skull anchoring device 504 or to another receiving port connected to the low profile skull anchoring device 504 (not illustrated).

The guide sheath 540, upon interlocking with the guide stem 506, 520 and/or the low profile skull anchoring device 504 and receiving one or more neurosurgical tools, may create an air-tight seal during a neurosurgical operation. For example, the proximal and/or distal end of the guide sheath 540 may include a receiving port adaptable to the surgical instrument being introduced. In certain embodiments, various guide sheaths can be used interchangeably with the guide stem 506, 520, such that a guide sheath corresponding to the surgical instrument diameter may be selected. In other implementations, one or more guide sleeves (not illustrated) may be secured inside the guide sheath 540, each of the one or more guide sleeves having a different distal end diameter. A divided (e.g., bifurcated) guide sleeve, in certain embodiments, may be used to introduce two or more instruments simultaneously or concurrently, each with a particular instrument diameter.

In certain embodiments, the guide sheath 540 is intracranially delivered using an introducer and guide wire. An image guidance system, such as the MRI imaging system, may be used instead of or in addition to the introducer and guide wire during placement of the guide sheath 540. The guide sheath 540 may be composed of MRI compatible materials.

The materials of the guide sheath 540, in certain embodiments, are selected to provide rigid or inflexible support during introduction of one or more neurosurgical tools within the guide sheath 540. For example, the guide sheath 540 may be composed of one or more of Kevlar, carbon fiber, ceramic, polymer-based materials, or other MRI-compatible materials. The geometry of the guide sheath 540, in certain embodiments, further enhances the strength and rigidity of the guide sheath 540.

Figure 5H:
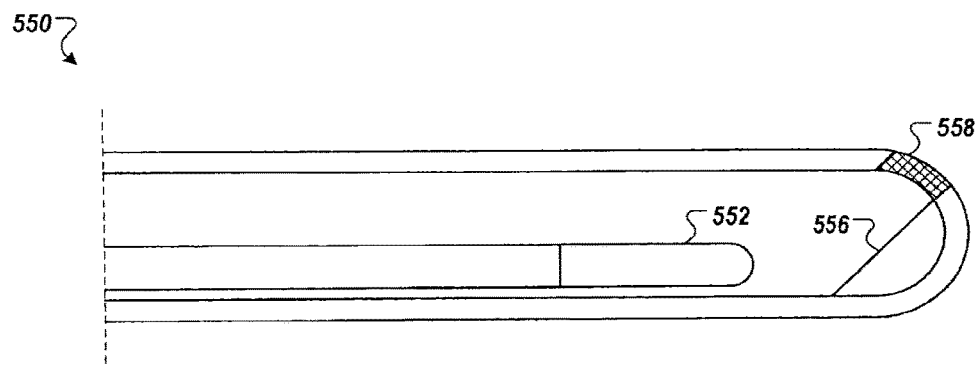
FIGS. 5H and 5I illustrate example internal configurations of a guide sheath.
Figure 5I:
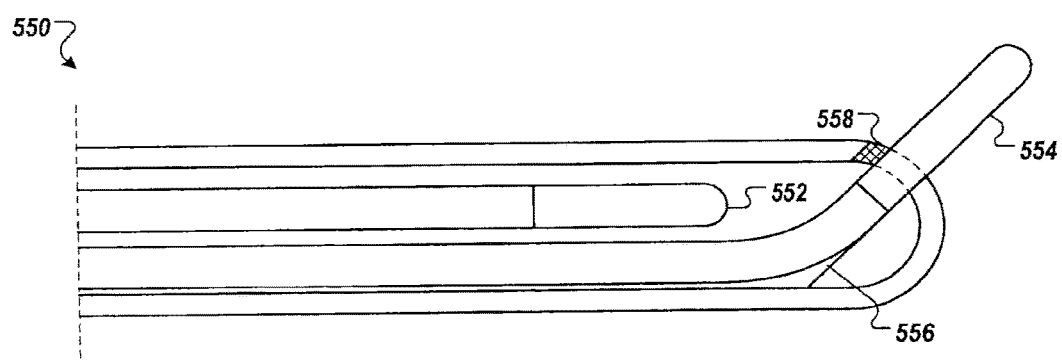

In certain embodiments, the guide sheath 540 (or guide sleeve, as described above) includes two or more lumens for introduction of various neurosurgical instruments. By introducing two or more neurosurgical instruments via the guide sheath 540, a series of treatments may be performed without interruption of the meninges layer between treatments. For example, FIG. 5I illustrates two neurosurgical instruments 552 and 554 that are simultaneously inserted into a guide sheath 550 and can be used to carry out treatment of a tissue consecutively, concurrently, or simultaneously.

Neurosurgical instruments deployed via the guide sheath 540 may exit a same distal opening or different distal openings. In certain embodiments, the guide sheath 540 may include at least one off-axis distal opening. For example, as illustrated in FIG. 5H, exemplary guide sheath 550 includes a contact surface 556 having a predefined angle. Upon encountering the contact surface 556, the trajectory of a surgical instrument 552 presented through the guide sheath 550 may be deflected to exit the proximal end via an off-axis delivery hole 558, as illustrated in FIG. 5I. The angles shown in FIGS. 5H and 5I can be considered as drawn to scale in one implementation. However, the alignment of the contact surface 556 and the delivery hole 558 can be varied by adjusting their respective axial angles. By adjusting these angles, a number of possible positions of the surgical instrument 554 are provided. Further, multiple off-axis delivery holes and multiple contact surfaces can be provided, which are displaced from each other in a direction of the longitudinal axis of the guide sheath.

Upon introducing a neurosurgical instrument such as a probe, in certain embodiments, the guide sheath 510 enables coupling between the probe and a probe actuation and guidance device. For example, commands for linear and/or rotational control of the probe may be issued to the probe via an interface within the guide sheath 540.

III. Probes

A number of different probes can be utilized in accordance with the various aspects presented in this disclosure. Example probes are described in: U.S. Pat. No. 8,256,430 to Torchia, entitled "Hyperthermia Treatment and Probe Therefor" and filed Dec. 17, 2007; U.S. Pat. No. 7,691,100 to Torchia, entitled "Hyperthermia Treatment and Probe Therefor" and filed Aug. 25, 2006; U.S. Pat. No. 7,344,529 to Torchia, entitled "Hyperthermia Treatment and Probe Therefor" and filed Nov. 5, 2003; U.S. Pat. No. 7,167,741 to Torchia, entitled "Hyperthermia Treatment and Probe Therefor" and filed Dec. 14, 2001; PCT/CA01/00905, entitled "MRI Guided Hyperthermia Surgery" and filed Jun. 15, 2001, published as WO 2001/095821; and U.S. patent application Ser. No. 13/838,310, entitled "Image-Guided Therapy of a Tissue" and filed Mar. 15, 2013. These documents are incorporated herein by reference in their entireties.

A number of probe lengths are provided in any of the probe examples described herein based on a degree of longitudinal travel allowed by a follower and a depth of the tissue to be treated. An appropriate probe length can be determined by the interface platform and/or the workstation during a planning stage, or determined during a trajectory planning stage.

Exemplary probe lengths can be indicated on the probes with reference to a probe shaft color, in which white can indicate "extra short" having a ruler reading of 113 mm, yellow can indicate "short" having a ruler reading of 134 mm, green can indicate "medium" having a ruler reading of 155 mm, blue can indicate "long" having a ruler reading of 176 mm, and dark gray can indicate "extra long" having a ruler reading of 197 mm. Different model numberings can also be utilized on the probes to indicate different lengths.

An energy output pattern of a probe, such as a laser probe or HIFU probe, in certain embodiments, includes a pulsed output pattern. For example, a higher power density may be achieved without causing tissue scorching by pulsing a high power laser treatment for x seconds with y seconds break between (e.g., allowing for tissue in the immediate vicinity to cool down). In a particular example, the energy output pattern of a probe may include a ten Watt output for two seconds followed by a one second period of inactivity. In certain embodiments, a particular energy output pattern may be developed based upon the type of probe (e.g., laser, HIFU, etc.), an emission style of the probe tip (e.g., side-firing, diffuse tip, etc.), and/or the depth of the ROI or the targeted tissue area (e.g., based in part on the shape of a tumor region, etc.).

In certain embodiments, a treatment pattern includes effecting treatment while concurrently or simultaneously moving the probe (e.g., linearly and/or rotationally). For example, a HIFU probe may be automatically rotated (e.g., using a commander and follower as described in FIG. 3, etc.) while an emission pattern is simultaneously or concurrently adjusted to effect treatment to a desired depth based upon a particular geometry of the ROI. In this manner, for example, while the ultrasonic probe's beam is focused on a radial portion of the tumor having a depth of 1.5 centimeters, the power density of the HIFU probe may be tuned for the first treatment depth. Upon rotation, a second radial portion of the tumor may have a depth of 2 centimeters, and the power density of the HIFU probe may be increased accordingly to tune for the treatment depth of 2 centimeters.

A. Side-Fire HIFU Probe

Figure 9A:
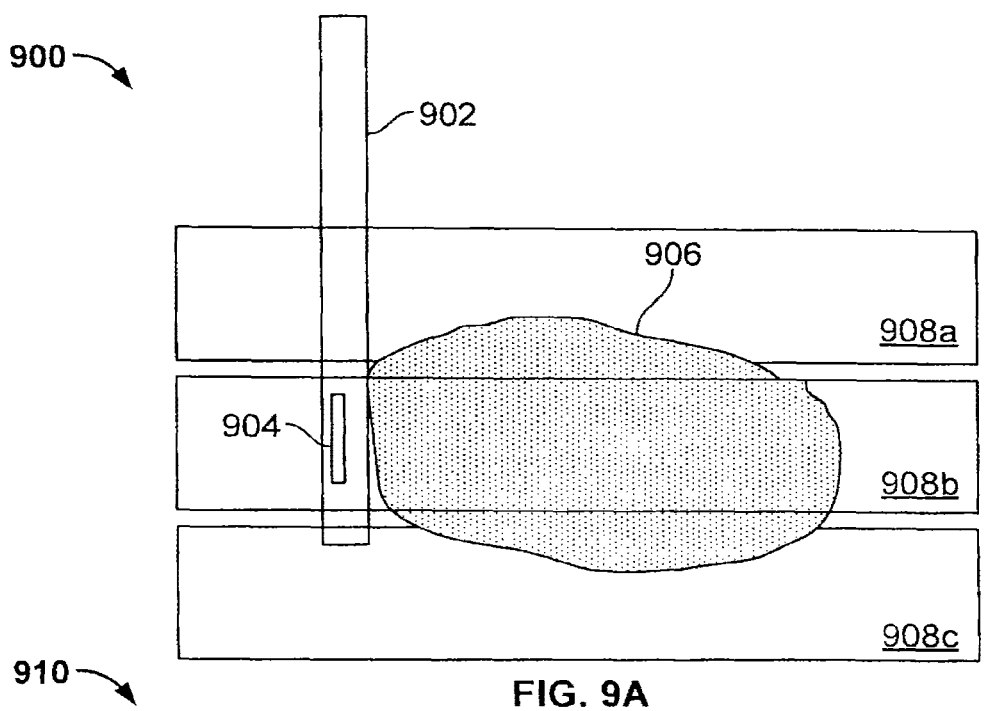
FIGS. 9A through 9C illustrate a high intensity focused ultrasound probe.
Figure 9B:
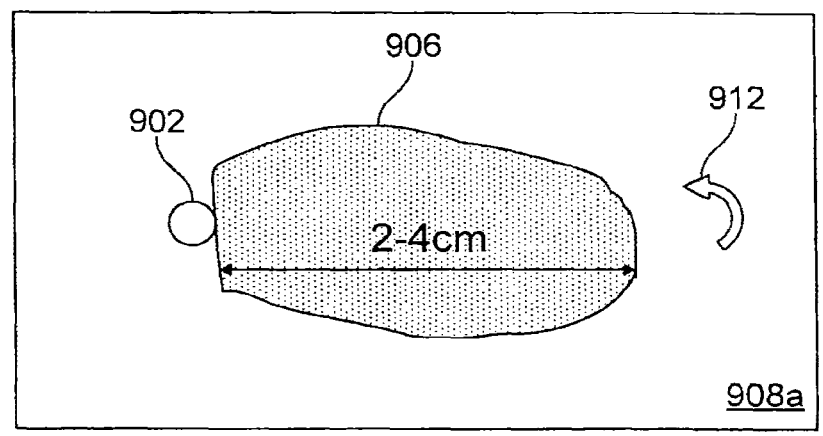

Turning to FIG. 9A, a view 900 of an exemplary treatment scenario involving a HIFU probe 902 deployed to treat an ROI 906 is illustrated. HIFU technology advantageously provides directional control and greater depth penetration as compared with laser-based thermal therapy. For example, in comparison to laser therapy, ultrasonic therapy may achieve at least three to four times greater depth penetration. For example, estimated depths of thermal treatment using HIFU technology include three to five centimeters or greater than six centimeters. By completing treatment via an initial trajectory, the treatment may be performed faster and less invasively than it may have been performed using a laser probe. As such, a HIFU probe may be used to treat a larger ROI without the need to adjust a probe trajectory or introduce the probe into multiple locations within the brain. Although treatment may be provided at a greater depth, it also may be provided using a narrow focal beam, containing a width of the treated tissue. Furthermore, although HIFU-based thermal therapy can advantageously achieve a greater penetration depth than laser-based thermal therapy, the ultrasonic treatment has greater uniformity over temperature gradients than laser-based thermal therapy, which heats a portion of the targeted tissue area close to the probe much more rapidly than portions of the targeted tissue area further away from the probe. In selecting thermal therapy via a HIFU probe, scorching or carbonization of the targeted tissue area close to the probe may be avoided and/or the HIFU probe may be operated independently of external cooling to protect immediately surrounding tissue.

In performing thermal therapy using a HIFU probe, constructive and destructive interference can be utilized by selecting a number of different longitudinal spaced emission points to fine tune a position and depth of energy applied to a targeted tissue area and/or an ROI. As such, the depth of energy, as such, may be tuned to conform with a non-uniform, irregular, and/or non-polygonal shape of the ROI which, for example, corresponds to a tumor. Preparing trajectories, determining linear translational adjustments and/or rotational movements, and/or energy output patterns may be selected and/or optimized to prevent heating of the skull and/or bouncing energy off of the surfaces of the skull. HIFU treatment, in some examples, can be used for opening a blood-brain barrier, coagulation of tissue, or cavitation of tissue.

Figure 9C:
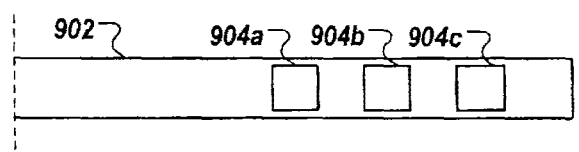

The HIFU probe 902 includes one or more side-firing transducers 904 for effecting treatment to the ROI 906. The ultrasonic transducer(s) 904 may be flat or rounded. The HIFU probe, in some examples, can include a shaft composed of plastic, brass, titanium, ceramic, polymer-based materials, or other MRI-compatible materials in which one or more ultrasonic transducer(s) 904 have been mounted. The ultrasonic transducer(s) 904 may be mounted upon an interior surface of the shaft of the HIFU probe 902. The ultrasonic transducer(s) 904 may include a linear array of individually controllable transducers, such that a frequency or power output of each transducer 904 may be individually tuned to control a treatment beam of the HIFU probe 902. For example, as illustrated in FIG. 9C, the tip of the probe 902 can include a linear array of three transducers 904. The longitudinally spaced apart transducers 904 can be spaced equally apart. However, in other implementations, the spacing between the transducers 904 can be unequal.

In certain embodiments, the HIFU probe 902 includes a cooling mechanism for cooling the ultrasonic transducers 904. For example, a cooling fluid or gas may be delivered to the tip of the HIFU probe 902 to control a temperature of the ultrasonic transducer(s) 904. Additionally, the ultrasonic transducer(s) 904 may be surrounded by an acoustic medium, such as an acoustic coupling fluid (e.g., water) to enable ultrasonic frequency tuning of the ultrasonic transducer(s) 904.

As illustrated in FIG. 9A, the HIFU probe 902 is embedded within an ROI 906 spanning multiple MR thermal monitoring planes 908. During treatment, thermal effects within each MR thermal monitoring plane 908 may be monitored in order to monitor thermal coagulation of the ROI 906. Information derived from the thermal monitoring, for example, may be fed back into control algorithms of the HIFU probe 902, for example, to adjust a power intensity and/or frequency of the HIFU probe to tune a depth of treatment of the ultrasonic beam or to adjust a rotational and/or linear positioning of the HIFU probe 902 upon determining that ablation is achieved at a current rotational and linear position.

To increase the monitoring region, additional MR thermal monitoring planes 908 may be monitored (e.g., between four and eight planes, up to twelve planes, etc.). Alternatively, in certain embodiments, the three thermal monitoring planes 908 may be spread out over the y-axis such that a first gap exists between plane 908a and plane 908b and a second gap exists between plane 908b and plane 908c. The thermal monitoring algorithm, in this circumstance, can interpolate data between the MR thermal monitoring planes 908.

In other implementations, rather than obtaining parallel images of MR thermal monitoring planes, at least three thermal monitoring planes, each at a distinct imaging angle bisecting an axis defined by a neurosurgical instrument such as a thermal ablation probe, may be interpolated to obtain thermal data regarding a three-dimensional region.

Turning to FIG. 10A, an aspect illustration 1000 demonstrates three MR thermal monitoring planes 1002 for monitoring ablation of an ROI 1004 by a probe 1006. The angles between the thermal monitoring planes, in some examples, may be based upon an anatomy of the region of the skull of the patient or a shape of the ROI. The angles, in some examples, may differ by at least ten degrees.

Turning to FIG. 10B, an end view 1010 of the probe 1006 provides an illustrative example of MR thermal monitoring planes 1002 that are each offset by sixty degrees. In comparison to using parallel MR thermal monitoring planes, the thermal monitoring planes 1002 provide a more realistic three-dimensional space. Thus, volumetric visualization is provided. In certain embodiments, volumetric visualization that independent of ablation is provided. Temperature gradients and/or thermal dose profiles between the thermal monitoring planes 1002 can be interpolated. Similar to increasing a number of parallel MR thermal monitoring planes, in other implementations, four or more thermal monitoring planes may be captured and combined, for example, to increase thermal monitoring accuracy.

As a result of the side-firing capability of the HIFU probe 902, a number of rotationally different portions of the ROI can be treated with the ultrasonic energy by rotating the HIFU probe 902. For example, as illustrated in an x-axis sectional view 910, the HIFU probe 902 may be rotated is illustrated in an arrow 912 to effect treatment throughout the ROI 906. Additionally, the HIFU probe 902 can be longitudinally translated, for example automatically by a follower of a probe driver, to change a longitudinal position at which ultrasonic energy is applied within the ROI 906.

Rotation, power intensity, duty cycle, longitudinal positioning, and cooling, in certain embodiments, are controlled by the electronics rack 104 and the workstation 106, such as the electronics rack 104 and workstation 106 described in relation to FIG. 1. A sequence, such as an algorithm or software encoding, can be executed to cause a probe tip or a number of probe tips to execute a particular energy output pattern effect a predefined thermal therapy to a targeted tissue area. The energy output pattern can be based on rotational and/or longitudinal movements of the probe.

B. Pre-Shaped Probe

Figure 8:
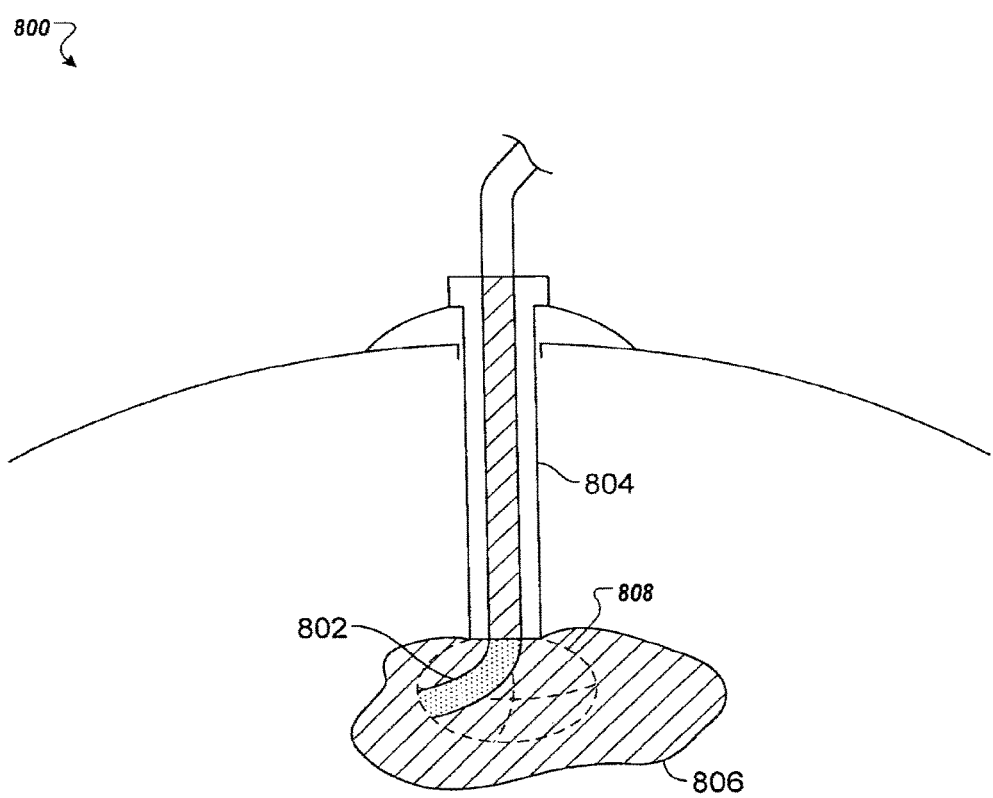
FIG. 8 is an illustration of a pre-shaped probe deployed from a rigid sheath.

Turning to FIG. 8, in certain embodiments, a probe delivery apparatus 800 includes a pre-shaped probe 802 (e.g., laser probe) that accesses an ROI 806 along a curved path. The pre-shaped probe 802 can be provided proximate to the ROI 806 through a rigid sheath 804 or guide cannula. Although the rigid sheath 804 is straight, the pre-shaped probe 802 is flexible such that it exits the rigid sheath 804 in a predetermined arc. The curvature of the pre-shaped probe 802, for example, can be configured to deploy towards a known radial position, for example in a quarter arc of a circle. In exiting the rigid sheath 804, the pre-shaped probe 802 follows a clean arc along a path into the ROI 806. In this manner, the pre-shaped probe 802 avoids tearing tissue, for example due to pushing a distal end of the probe against the targeted tissue area and/or an ROI.

In certain embodiments, the pre-shaped probe 802 includes a wire and/or polymer encasement for a laser fiber. The materials of the pre-shaped probe 802, for example, may prevent the laser probe (and optical fiber corresponding thereto) from straightening, which is its natural inclination. The pre-shaped probe 802, in certain embodiments, is composed of MRI-compatible materials to enable use in MRI-guided neurosurgery. In one example, the pre-shaped probe may include a polymer tubing with a pre-curved band to the probe tip, surrounding a laser fiber. In certain embodiments, a tip region of the pre-shaped probe 802 includes at least one fiducial marker to aid in validating an angle of deployment from the rigid sheath 804.

During thermal therapy, the pre-shaped probe 802, in certain embodiments, may be deployed into the ROI 806 at a first location, then withdrawn into the rigid sheath 804, rotated, and deployed into the ROI 806 at a different radial location. A range outline 808 demonstrates a rotational range of the pre-shaped probe 802 at a current linear position. Rotational adjustment of the pre-shaped probe 802 may be repeated a number of times, for example to effect treatment spanning substantially a full rotational range 808. Additionally, upon withdrawal, the rigid sheath 804 may be made linearly adjusted (e.g., manually or automatically using a probe driver) and the pre-shaped probe 802 deployed in a different linear region at the same or a different rotational projection.

In some examples, a length of the rigid sheath 804 can be approximately twelve to fifteen centimeters, and a diameter of the rigid sheath 804 can be approximately three-tenths of a centimeter to one centimeter. A diameter of the pre-shaped probe 802 can be one-tenth of a millimeter to three millimeters. A curved extension of the pre-shaped probe, for example, may be about one to two centimeters. The pre-shaped probe 802 can include one or more energy delivery elements. For example, the pre-shaped probe may include a diffuse laser emission tip. In certain embodiments, the pre-shaped probe 802 includes a cooling element. Examples of energy element and cooling element configurations of laser probes are illustrated, for example, in U.S. patent application Ser. No. 13/838,310 to Tyc, filed Mar. 14, 2013 and titled "Image-Guided Therapy of a Tissue," incorporated herein by reference in its entirety.

In certain embodiments, additional neurosurgical instruments may be provided to the ROI 806 via the rigid sheath 804 along with the pre-shaped probe 802. For example, the pre-shaped probe 802 may be positioned within the rigid sheath 804 along with other probes to be used consecutively, contemporaneously, simultaneously or concurrently with the pre-shaped probe 802.

IV. Head Coil and Stabilization

Prior to positioning in an MRI bore, a head fixation ring is attached to the patient's head to ensure a fixed position during the thermal therapy. A standard fixation ring can be problematic, both in fitting various sizes of patients and in the difficulty of positioning the patient within the ring. For example, patients with spinal deformation or unusually large heads (e.g., due to steroid treatments) may be difficult to position within the standard fixation ring, which is pre-formed.

Turning to FIG. 6A, rather than using a standard size fixation ring for fixating a patient's head, a head fixation system 600 includes an upper ring portion 602 and a lower ring portion 604. A patient's head may be laid upon the lower ring portion 604, and the upper ring portion 602 may be lowered and connected to the lower ring portion 604 such that the patient's nose is aligned with an indent 606 of the upper ring portion 602.

In certain embodiments, the upper ring portion 602 connects with the lower ring portion 604 in an adjustable fashion, providing for a secure and close fit for a variety of head sizes. In other embodiments, various sizes of upper ring portions 602 may be provided, such that, rather than connecting to form a circular ring, each upper ring portion extends to form an ovoid shape of the head fixation system 600 to a different length.

As illustrated in FIG. 6A, the lower ring portion 604 includes a number of support posts 608 for aiding in fixation of the head. The support posts 608, in certain embodiments, are selectively positioned in a number of support post mounting slots 610 arranged radially along both the upper ring portion 602 and the lower ring portion 604. As illustrated, there are six support post mounting slots 610 arranged on the upper ring 602 and seven support post mounting slots 610 arranged on the lower ring 604. In other implementations (not illustrated), the support posts 608 are mounted in fixed positions upon one or both of the upper ring portion 602 and the lower ring portion 604. The number of support post mounting slots 610 may vary. Additionally, in another embodiment, the support posts 608 may selectively mount by two or more pegs or posts connected to each support post 608 rather than by a single connection point (e.g., support post mounting slot 610).

The support posts 608 can be used to introduce a number of fasteners, such as a set of skull pins 612a and 612b, for affixing the ring portions 602, 604 to the head of the patient. As illustrated, each support post 608 includes a series of four pin mounts for mounting a skull pin 612. In another example, each support post 608 may include a number of offset pin mounts (not illustrated), such that the pin mounts will not necessarily be centered upon the support post. In this manner, the medical professional may adjust both radial pinning locations via the support post mounting slots 610 and linear pinning locations via the pin mounts of each support post 608 to adaptably secure a patient within the head fixation system 600. In other implementations, rather than using pins, a passive fixation system can provide conforming abutments, such as formable pads, for closely securing the head of the patient within the head fixation system 600 without the use of pins 612. The conforming abutments, in one embodiment, are fixedly mounted to each support post 608. In other embodiments, the conforming abutments may be releasably connected in a manner similar to the fixation pins 612.

Figure 6D:
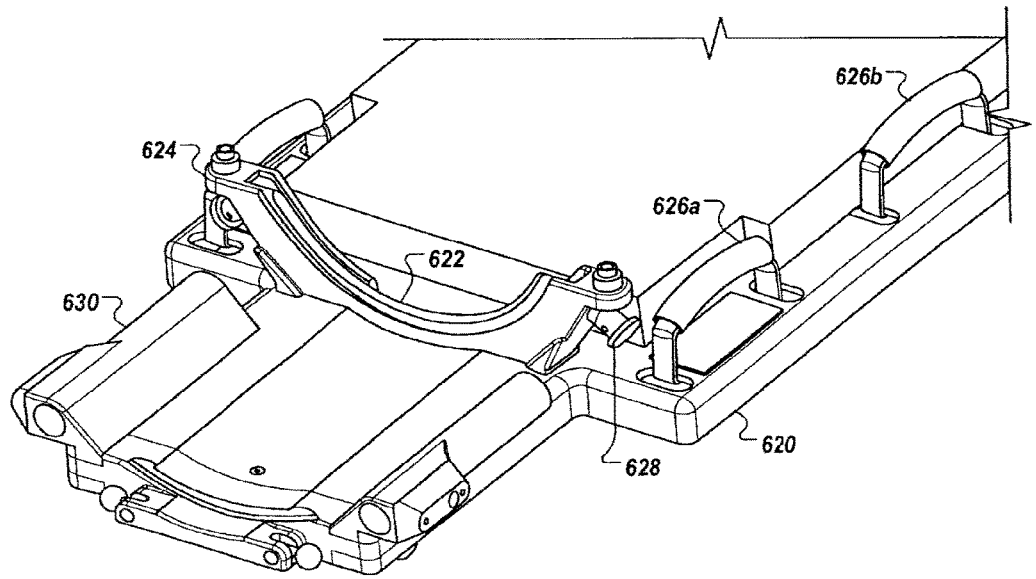
FIGS. 6D and 6E illustrate a mounting location on an MRI platform for the head fixation system of FIGS. 6A and 6B.
Figure 6E:
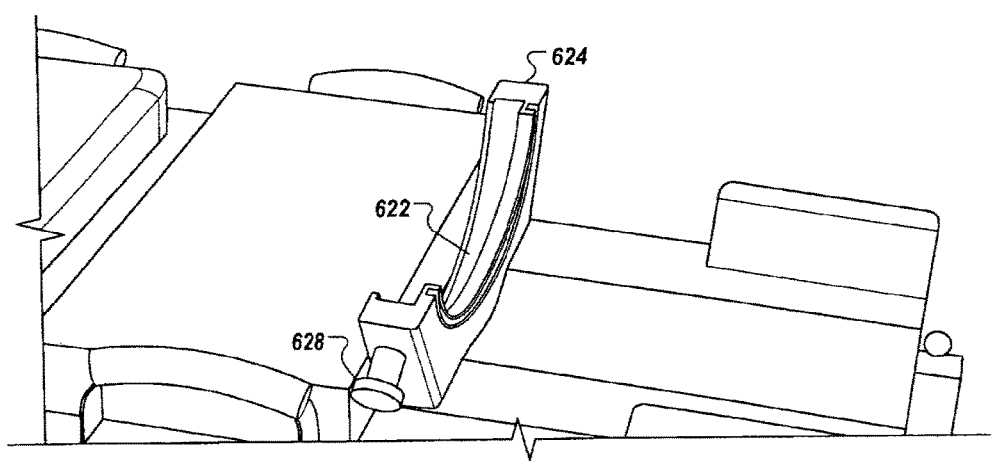

A patient's head can be positioned into the lower ring portion 604 and onto skull pins 612. The lower ring portion 604, for example, may be mounted within a channel 622 of a ring mount 624 of a platform 620, as illustrated in FIGS. 6D and 6E. The upper ring portion 602 may then be lowered into place, connecting with the lower ring portion 604 (e.g., at mating points 616 and 618). The mating points 616 and 618, in certain embodiments, include spaced indentations or openings for interfacing with a locking mechanism such as a set screw or spring-loaded plunger. In other implementations, the head fixation system 600 may have spaced ratcheting teeth on one of the ring portions 602, 604 for interfacing with a ball plunger or toggle release mounted on the other ring portion 602, 604. In further implementations, a linear actuator system such as a rack and pinion may be used to provide position adjustment (e.g., one "click" per linear setting), lockable, for example, using a cam lock.

Positions of the support posts 608 and/or skull pins of the upper ring portion 602 may be adjusted. When a desired positioning has been achieved, the upper ring portion 602 may be locked to the lower ring portion 604, as illustrated in FIG. 6B.

Turning to FIG. 6C, in a particular example, a locking mechanism 614 demonstrates that the upper ring portion 602 may lock to the lower ring portion 604 using keyed shapes secured with a fastener, such as a thumb screw. After locking the upper ring portion 602 to the lower ring portion 604, the skull pins can be tightened to achieve appropriate fixation. At this point, in certain embodiments, the patient can be wheeled upon the platform 620 to an MRI room, where users can utilize the handles 626 to move the fixated patient from, e.g., a wheeled operating table to an MRI table. In other implementations, the platform is part of the MRI table, for example as illustrated in FIG. 2. The fixation system 600 may be locked to the ring mount 624 via knobs 628.

In certain embodiments, upon positioning the head fixation system 600 into the ring mount 624, an angle of the head of the patient can be adjusted. For example, turning to FIG. 6D, the head fixation system 600 (not illustrated) may be rotated within the channel 622 (e.g., up to fifty degrees to either the left or the right) prior to locking the head fixation system 600 into the ring mount 624 via the knobs 628.

The head fixation system 600, in certain embodiments, includes one or more fiducial markers used, for example, to identify a position or type of head fixation ring. For example, if the upper ring portion 602 is one of a set of various radiuses of upper ring portions, one or more fiducial markers may identify the particular upper ring portion 602 selected. In another example, one or more fiducial markers can be used to identify an angle of rotation of the head fixation system 600 from a central position (e.g., nose indent 606 pointing upwards. The fiducial markers, in a particular example, may be arranged radially upon an exterior of at least one of the upper ring portion 602 and the lower ring portion 604) for aiding in registration of an MR image. Furthermore, the fiducial markers may be used by a software tool to provide modeling for the head fixation system 600 in relation to an instrument introduction apparatus, neurosurgical instruments, and/or other medical equipment used during the neurosurgical procedure. The fiducial markers, for example, may provide the software with an indication of angle of rotation of the head of the patient.

After attaching the head fixation system 600 to the patient, a head coil can be fixed to the head fixation system 600 and/or a head coil support 630. For example, turning to FIG. 2, a patient is arranged on a patient table 108 in a bore of the MRI system 110. The patient's head 210 is fixed to a head fixation ring 204 by fixation pins. The head fixation ring 204 is received in a ring mount of the patient table 108, for example the ring mount 624 illustrated in FIG. 6E. The patient table 108 extends, in a direction away from the bore of the MRI system 110, providing a head coil support.

Figure 7:
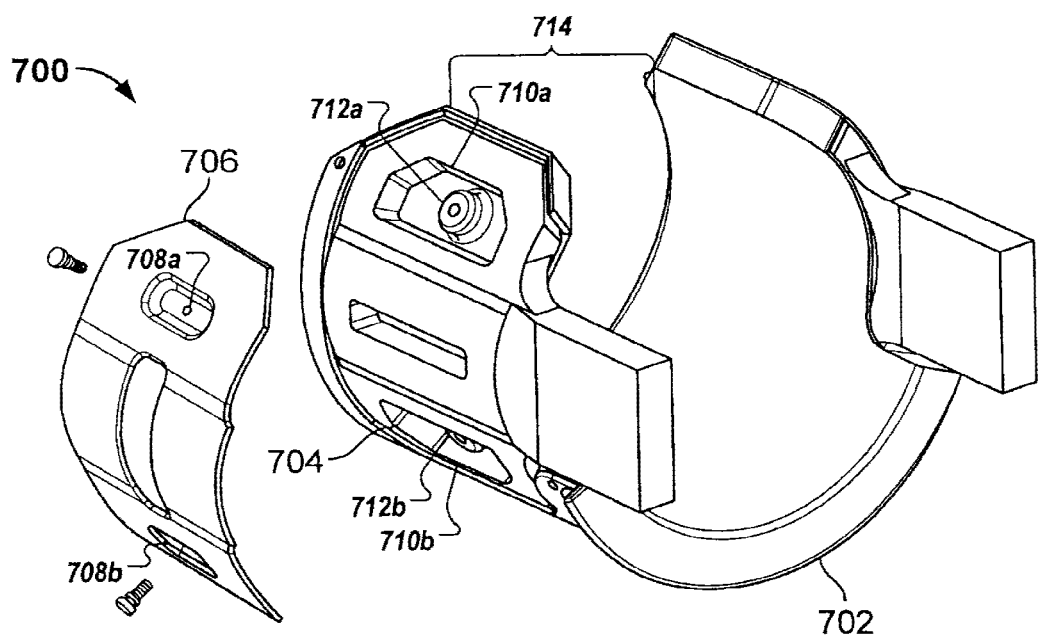
FIG. 7 is an illustration of an MRI coil holder.

Turning to FIG. 7, a head coil system 700 including a coil holder 702 that accommodates various off-the-shelf MRI coils, such as an MRI coil 704 is illustrated. The coil holder 702, for example, can include adjustable attachment points for attaching the MRI coil 704 to the coil holder 702. The adjustable attachment points, for example, can include mated fastener openings 708, 710 between a cover 706 and the coil 704. The cover 706, for example, may align over the MRI coil 704 such that fastener openings 708 in the cover 706 align with fastener openings 710 within the coil 704 to hold the coil 704 in place against the coil holder 702. The MRI coil 704 may be aligned with openings in the MRI coil 704 positioned to expose one or more fastener attachment points 712. The user may then secure the MRI coil 704 to the coil holder 702 by attaching fasteners through the fastener openings 708, 710 of the cover 706 to fastener attachment points 712 upon the coil holder 702. Any number of fastener openings 708, 710 and fastener attachment points 712 can be included the head coil system 700 to accommodate a variety of off-the-shelf MRI coils, such that the coil holder 702 and cover 706 provide a "universal" attachment system for a number of styles and/or brands of off-the-shelf MRI coils. In other implementations, rather than including fastener openings 708, 710 in the cover 706 and fastener attachment points 712 upon the coil holder 702, the cover 706 may mateably engage with the coil holder 702. For example, upon positioning the MRI coil 704 within the coil holder 702, the cover 706 may be slid into mating grooves and snapped into place, securing the MRI coil 704. In another example, latches or clips formed into one of the coil holder 702 and the cover 706 may mate to opposing connection points on the other of the coil holder 702 and the cover 706. Rather than the cover 706, in certain embodiments, two or more attachment bands or sections may releasably attach to the coil holder 702 (e.g., in a manner described above in relation to the cover 706), securing the MRI coil 704 in place.

The head coil system 700, in certain embodiments, includes openings that provide access for neurosurgical instruments, such as an opening 714. A user can adjust the openings to align the openings with a desired trajectory. Due to the open structure of the head coil system 700, while a patient is positioned within the head coil system 700, a surgical team has access to a wide variety of trajectories for performing neurosurgical operations, such as a trajectory at or near a side to forehead region of the patient's head, a trajectory at a side of the patient's head, or a trajectory at the top of the patient's head. The components of the head coil system 700 are easily released to incorporate different MRI coils.

After the user has achieved a desired alignment and positioned the patient within the MRI bore with the head coil system 700, the user can connect the head coil system 700 to a cable to energize the MRI coil 704. Further, the user can drape the patient and attach probe introduction equipment, such as a miniframe or low profile skull anchor and guide. Due to a smooth inner surface of the head coil system 700, surgical draping of the patient is simplified.

The procedures and routines described herein can be embodied as a system, method or computer program product, and can be executed via one or more dedicated circuits or programmed processors. Accordingly, the descriptions provided herein may take the form of exclusively hardware, exclusively software executed on hardware (including firmware, resident software, micro-code, etc.), or through a combination of dedicated hardware components and general processors that are configured by specific algorithms and process codes. Hardware components are referred to as a "circuit," "module," "unit," "device," or "system." Executable code that is executed by hardware is embodied on a tangible memory device, such as a computer program product. Examples include CDs, DVDs, flash drives, hard disk units, ROMs, RAMs and other memory devices.

Figure 11:
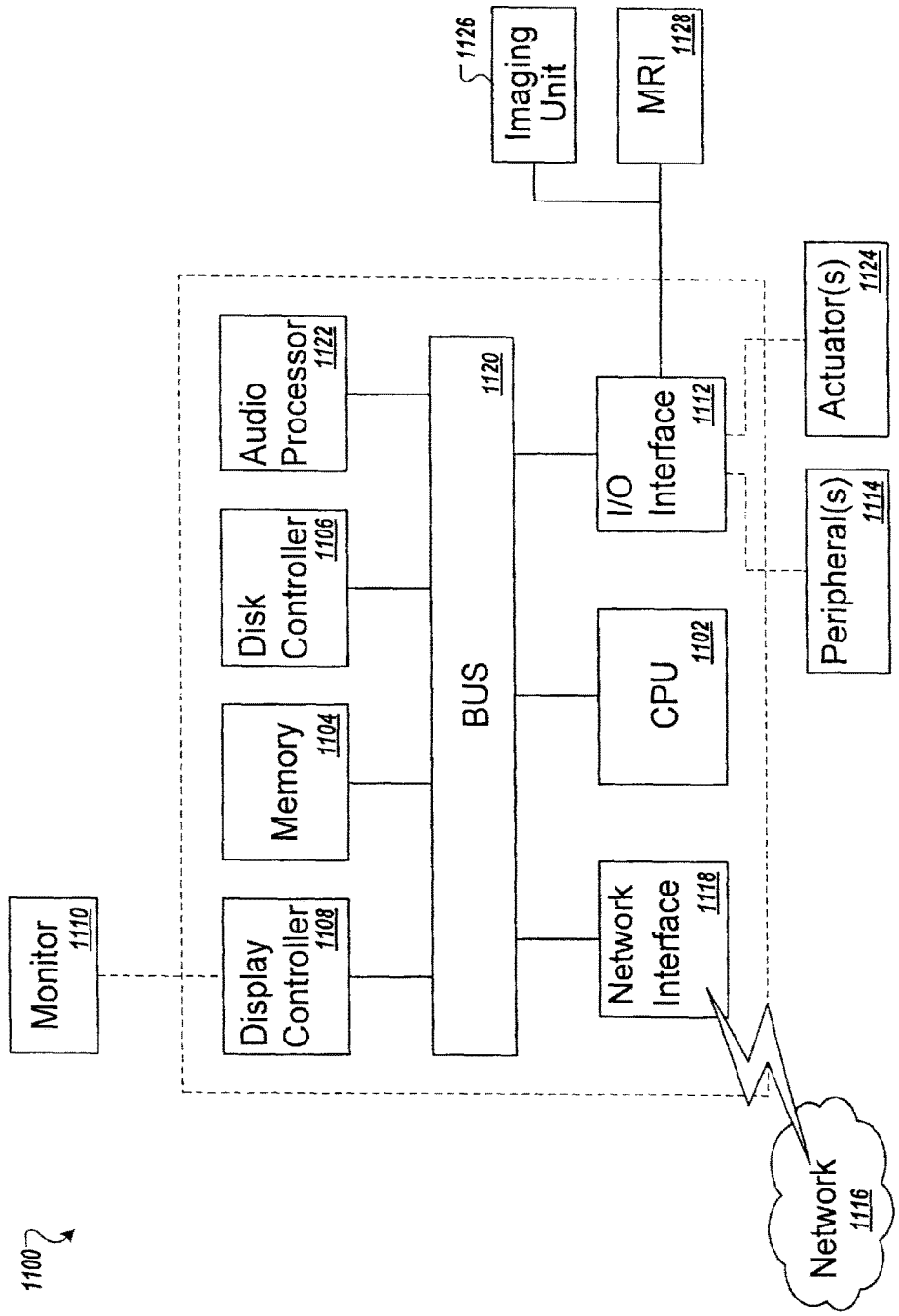
FIG. 11 illustrates exemplary hardware of a workstation.

FIG. 11 illustrates an exemplary processing system 1100, and illustrates example hardware found in a controller or computing system (such as a personal computer, i.e., a laptop or desktop computer, which can embody a workstation according to this disclosure) for implementing and/or executing the processes, algorithms and/or methods described in this disclosure. The processing system 1100 in accordance with this disclosure can be implemented in one or more the components shown in FIG. 1. One or more processing systems can be provided to collectively and/or cooperatively implement the processes and algorithms discussed herein.

As shown in FIG. 11, the processing system 1100 in accordance with this disclosure can be implemented using a microprocessor 1102 or its equivalent, such as a central processing unit (CPU) and/or at least one application specific processor ASP (not shown). The microprocessor 1102 is a circuit that utilizes a computer readable storage medium 1104, such as a memory circuit (e.g., ROM, EPROM, EEPROM, flash memory, static memory, DRAM, SDRAM, and their equivalents), configured to control the microprocessor 1102 to perform and/or control the processes and systems of this disclosure. Other storage mediums can be controlled via a controller, such as a disk controller 1106, which can controls a hard disk drive or optical disk drive.

The microprocessor 1102 or aspects thereof, in alternate implementations, can include or exclusively include a logic device for augmenting or fully implementing this disclosure. Such a logic device includes, but is not limited to, an application-specific integrated circuit (ASIC), a field programmable gate array (FPGA), a generic-array of logic (GAL), and their equivalents. The microprocessor 1102 can be a separate device or a single processing mechanism. Further, this disclosure can benefit from parallel processing capabilities of a multi-cored CPU.

In another aspect, results of processing in accordance with this disclosure can be displayed via a display controller 1108 to a display device (e.g., monitor) 1110. The display controller 1108 preferably includes at least one graphic processing unit, which can be provided by a number of graphics processing cores, for improved computational efficiency. Additionally, an I/O (input/output) interface 1112 is provided for inputting signals and/or data from microphones, speakers, cameras, a mouse, a keyboard, a touch-based display or pad interface, etc., which can be connected to the I/O interface as a peripheral 1114. For example, a keyboard or a pointing device for controlling parameters of the various processes and algorithms of this disclosure can be connected to the I/O interface 1112 to provide additional functionality and configuration options, or control display characteristics. An audio processor 1122 may be used to process signals obtained from I/O devices such as a microphone, or to generate signals to I/O devices such as a speaker. Moreover, the display device 1110 can be provided with a touch-sensitive interface for providing a command/instruction interface.

The above-noted components can be coupled to a network 1116, such as the Internet or a local intranet, via a network interface 1118 for the transmission or reception of data, including controllable parameters. A central BUS 1120 is provided to connect the above hardware components together and provides at least one path for digital communication there between.

The workstation shown in FIG. 1 can be implemented using one or more processing systems in accordance with that shown in FIG. 11. For example, the workstation can provide control signals to peripheral devices attached to the I/O interface 1112, such as actuators 1124 to drive probe positioning and actuation equipment. The workstation, in certain embodiments, can communicate with additional computing systems, such as an imaging unit 1126 and/or an MRI unit 1128, via the I/O interface 1112.

One or more processors can be utilized to implement any functions and/or algorithms described herein, unless explicitly stated otherwise. Also, the equipment rack and the interface platform each include hardware similar to that shown in FIG. 11, with appropriate changes to control specific hardware thereof.

Reference has been made to flowchart illustrations and block diagrams of methods, systems and computer program products according to implementations of this disclosure. Aspects thereof are implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

A number of implementations have been described. Nevertheless, it will be understood that various modifications may be made without departing from the spirit and scope of this disclosure. For example, preferable results may be achieved if the steps of the disclosed techniques were performed in a different sequence, if components in the disclosed systems were combined in a different manner, or if the components were replaced or supplemented by other components. The functions, processes and algorithms described herein may be performed in hardware or software executed by hardware, including computer processors and/or programmable circuits configured to execute program code and/or computer instructions to execute the functions, processes and algorithms described herein. Additionally, certain embodiments may be performed on modules or hardware not identical to those described. Accordingly, other implementations are within the scope that may be claimed.

The invention claimed is:

1. A system for delivering intracranial energy emission therapy comprising: a probe for delivering intracranial energy emission therapy to a patient;

a probe driver including a commander unit and a follower for receiving the probe the follower operably coupled to the commander unit and configured to control a rotational and longitudinal movement of the probe within the patient;

an interface platform operably coupled to and configured to monitor the probe and probe driver; a head fixation device including a plurality of support posts for supporting a head of the patient, a curved ring portion including a lower ring portion, the curved ring portion comprising a plurality of connectors configured to adjustably and releasably mount the plurality of support posts on the lower ring portion, such that the plurality of support posts are selectively mounted to a subset of the plurality of connectors in a customized arrangement for the patient, a ring mount configured for fixation to a platform, wherein the ring mount comprises a curved channel substantially matching a curvature of the curved ring portion and a mount locking mechanism for locking the curved ring portion mounted within the channel of the ring mount, wherein, the curved ring portion is configured to rotate within the channel of the ring mount while the ring mount is fixed to the platform, an angular head position of the patient being selectively adjustable while the patient is laying on the platform, and the mount locking mechanism is configured to lockably engage the curved ring portion within the channel of the ring mount upon positioning of the angular head position of the patient; and a workstation operably coupled to the probe and configured to output signals to an MRI system to initiate imaging tasks associated with the delivery of the intracranial energy emission therapy by the probe.

2. The system of claim 1 wherein the system is indicated for use to ablate, necrotize, carbonize and/or coagulate a targeted intracranial tissue.

3. The system of claim 1 wherein said probe is configured to deliver HIFU thermal therapy to the patient.

4. The system of claim 1 wherein said probe is a laser probe configured to deliver laser-based thermal therapy to the patient.

5. The system of claim 4 wherein the laser-based thermal therapy includes light from the ultraviolet, visible, near-infrared, mid-infrared and far-infrared spectrums.

6. The system of claim 4 wherein said laser probe is selected from gas lasers, chemical lasers, dye lasers, metal-vapor lasers, solid-state lasers, semiconductor lasers and free electron lasers.

7. The system of claim 1 wherein the longitudinal movement of the probe is from 20 mm to 150 mm.

8. The system of claim 1 wherein the rotational movement of the probe is from 300 degrees to 360 degrees.

* * * * *